(12) United States Patent
Chen et al.

(10) Patent No.: US 7,718,421 B2
(45) Date of Patent: May 18, 2010

(54) SAMPLE PROCESSING

(75) Inventors: Shuqi Chen, Brookline, MA (US);
Bertrand Lemieux, Brighton, MA (US);
Zihua Wang, Newton, MA (US); Kevin R. Kopczynski, Cambridge, MA (US);
Lingjun Chen, Brookline, MA (US)

(73) Assignee: IQuum, Inc., Marlborough, MA (US)

( * ) Notice: Subject to any disclaimer, the term of this patent is extended or adjusted under 35 U.S.C. 154(b) by 1464 days.

(21) Appl. No.: 10/773,775

(22) Filed: Feb. 5, 2004

(65) Prior Publication Data

US 2004/0161788 A1    Aug. 19, 2004

Related U.S. Application Data

(60) Provisional application No. 60/445,304, filed on Feb. 5, 2003.

(51) Int. Cl.
*C12M 1/36* (2006.01)
(52) U.S. Cl. .................. 435/288.5; 206/219; 435/286.7; 435/299.2; 435/304.2; 435/810; 436/518
(58) Field of Classification Search .................. None
See application file for complete search history.

(56) References Cited

U.S. PATENT DOCUMENTS

| | | |
|---|---|---|
| 3,036,894 A | 5/1962 | Forestiere .................. 23/230 |
| 3,441,205 A | 4/1969 | Young, Jr. |
| 3,736,933 A | 6/1973 | Szabo |
| 4,065,263 A | 12/1977 | Woodbridge, III |
| 4,187,861 A | 2/1980 | Heffernan |
| 4,427,580 A | 1/1984 | Kinsella et al. |
| 4,483,920 A | 11/1984 | Gillespie et al. |
| 5,229,297 A | 7/1993 | Schnipelsky et al. |
| 5,234,809 A | 8/1993 | Boom et al. |
| 5,380,665 A * | 1/1995 | Cusack et al. .................. 436/53 |
| 5,422,271 A * | 6/1995 | Chen et al. ................ 435/287.2 |
| 5,705,628 A | 1/1998 | Hawkins |
| 5,811,296 A | 9/1998 | Chemelli et al. |
| 5,863,502 A | 1/1999 | Southgate |
| 5,898,071 A | 4/1999 | Hawkins |

(Continued)

FOREIGN PATENT DOCUMENTS

EP          0047806          3/1982

(Continued)

OTHER PUBLICATIONS

U.S. Appl. No. 10/920,134, filed Aug. 16, 2004, Chen, Shuqi.

(Continued)

*Primary Examiner*—N. C. Yang
(74) *Attorney, Agent, or Firm*—Scott E. Kamholz; Foley Hoag LLP

(57) ABSTRACT

A sample processing tubule may include a first segment, a second segment, and a third segment. Each segment may be defined by the tubule, may be fluidly isolated, at least in part by a breakable seal, may be so expandable as to receive a volume of fluid expelled from another segment, and may be so compressible as to contain substantially no fluid when so compressed. Each segment may contain at least one reagent.

63 Claims, 7 Drawing Sheets

U.S. PATENT DOCUMENTS

| | | | |
|---|---|---|---|
| 6,016,683 | A | 1/2000 | Betts |
| 6,068,751 | A | 5/2000 | Neukermans |
| 6,251,660 | B1 | 6/2001 | Muir et al. |
| 6,300,138 | B1 | 10/2001 | Gleason et al. |
| 6,318,191 | B1 | 11/2001 | Chen ................... 73/863.11 |
| 6,426,230 | B1 | 7/2002 | Feistel |
| 6,471,069 | B2 | 10/2002 | Lin et al. |
| 6,488,894 | B1 * | 12/2002 | Miethe et al. ............... 422/100 |
| 6,534,262 | B1 | 3/2003 | McKernan et al. |
| 6,748,332 | B2 | 6/2004 | Chen ..................... 702/19 |
| 6,780,617 | B2 | 8/2004 | Chen ..................... 435/91.2 |
| 7,198,759 | B2 * | 4/2007 | Bryning et al. ............ 422/100 |
| 2002/0192677 | A1 * | 12/2002 | Dimond et al. ............. 435/6 |
| 2003/0049833 | A1 * | 3/2003 | Chen et al. ............. 435/287.2 |
| 2003/1013439 | * | 7/2003 | Presnell et al. ........... 435/69.52 |
| 2004/0105782 | A1 | 6/2004 | Chen ..................... 422/60 |
| 2004/0189311 | A1 * | 9/2004 | Glezer et al. ............. 324/444 |
| 2004/0223878 | A1 | 11/2004 | Chen ..................... 422/68.1 |

FOREIGN PATENT DOCUMENTS

| | | |
|---|---|---|
| EP | 0435380 | 12/1990 |
| WO | WO 00/23803 | 4/2000 |
| WO | WO 01/07892 | 2/2001 |
| WO | WO 03/007677 A2 | 1/2003 |

OTHER PUBLICATIONS

European Search Report in EP02775793, mailed Sep. 17, 2009.

* cited by examiner

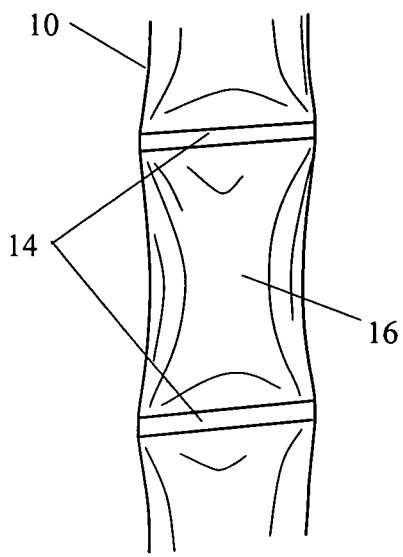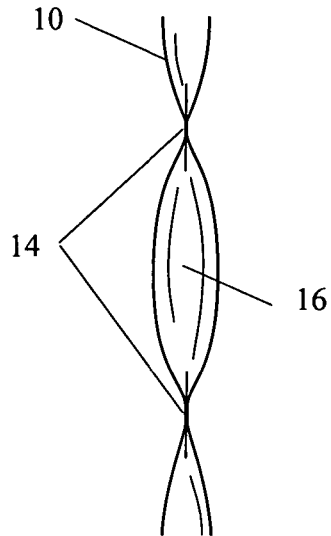
Fig. 3A  Fig. 3B
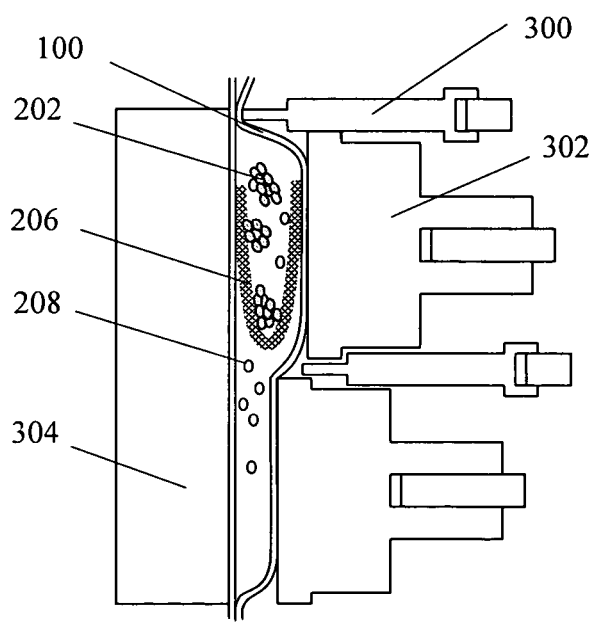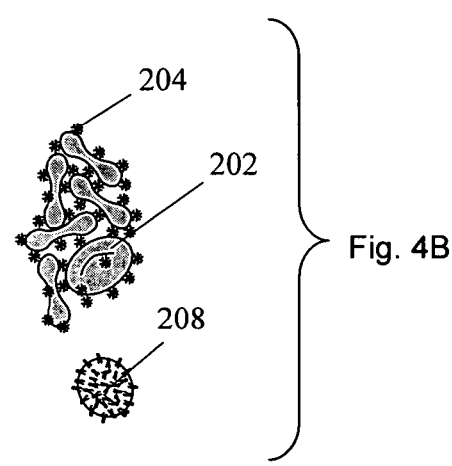
Fig. 4A  Fig. 4B

SAMPLE PROCESSING

CROSS-REFERENCE TO RELATED APPLICATION

This application claims the benefit of U.S. Provisional Patent Application Ser. No. 60/445,304, filed Feb. 5, 2003, which is hereby incorporated herein by reference in its entirety. The following U.S. patent applications are also hereby incorporated herein by reference in their entireties: Ser. Nos. 09/910,233; 09/782,732; and 10/241,816.

STATEMENT REGARDING FEDERALLY SPONSORED RESEARCH OR DEVELOPMENT

At least some of the disclosed subject matter was developed with government support under grant numbers 2R44HL67568-02, 1R43AI55079-01, and 1R43HL074689-01 awarded by the National Institutes of Health and contract number DAAD13-03-C-0086 awarded by the Department of Defense. The government may have certain rights in some of the disclosed subject matter.

INTRODUCTION

Sample preparation is frequently required in performing diagnostic assays, particularly in the processing of biological samples. A biological sample, for instance, typically undergoes intensive, demanding processing before it is in condition suitable for an assay. Proper sample preparation often requires precise conditions, such as particular temperatures, concentrations, reagent volumes, and, especially, the removal of materials that can interfere with the desired assay. Frequently a raw sample must be removed to a distant location to receive proper processing by highly skilled personnel in a tightly controlled laboratory setting. Conventional processing devices and methods often require large, highly complex and sophisticated instrumentation. These factors of conventional sample processing necessarily cause a delay in the time to result, high costs, compromised sample integrity and limitations on the practicality of using diagnostic assays in many instances.

SUMMARY

The present disclosure provides devices and methods for processing samples. The disclosed devices and methods can facilitate the preparation of samples through multiple processing steps.

In one aspect, a sample processing tubule may include a first segment, a second segment, and a third segment. Each segment may be defined by the tubule, may be fluidly isolated, at least in part by a breakable seal, may be so expandable as to receive a volume of fluid expelled from another segment, and may be so compressible as to contain substantially no fluid when so compressed. Each segment may contain at least one reagent.

In another aspect, a method of processing a sample may include introducing a sample into a tubule discretized by breakable seals into a plurality of fluidly isolated segments, wherein the tubule has a proximal end for receiving waste and a distal end for conducting an assay; incubating the sample in a segment of the tubule with a substance capable of specific binding to a preselected component of the sample; removing waste from the preselected component by clamping the tubule distally of the segment containing the preselected component and compressing that segment; and releasing a reagent to mix with the preselected component from a fluidly isolated adjacent distal segment by compressing at least one of the segment containing the preselected component and a segment containing a reagent distal of that segment, thereby opening a breakable seal and either propelling the reagent into the segment containing the preselected component or propelling the preselected component into the segment containing the reagent.

The disclosed devices and methods can provide significant advantages over the existing art. In certain embodiments, a tubule may be prepackaged with reagents for a desired sample processing protocol, thereby providing the materials for an entire assay in one convenient package. In certain embodiments, waste products are segregated from a target of interest early in the processing, so that the processed sample does not come into contact with surfaces that have been touched by the unprocessed sample. Consequently, trace amounts of reaction inhibitors present in the unprocessed sample that might coat the walls of the tubule are less likely to contaminate the processed sample.

BRIEF DESCRIPTION OF THE DRAWINGS

FIGS. 3A-B are, respectively, front and side elevation views of an exemplary embodiment of a sample tubule.

FIG. 4A is a cross sectional view of an exemplary embodiment of a sample tube positioned in an analyzer. FIG. 4B is a schematic close-up view of an embodiment of a biological sample.

DETAILED DESCRIPTION

Figure 1A:
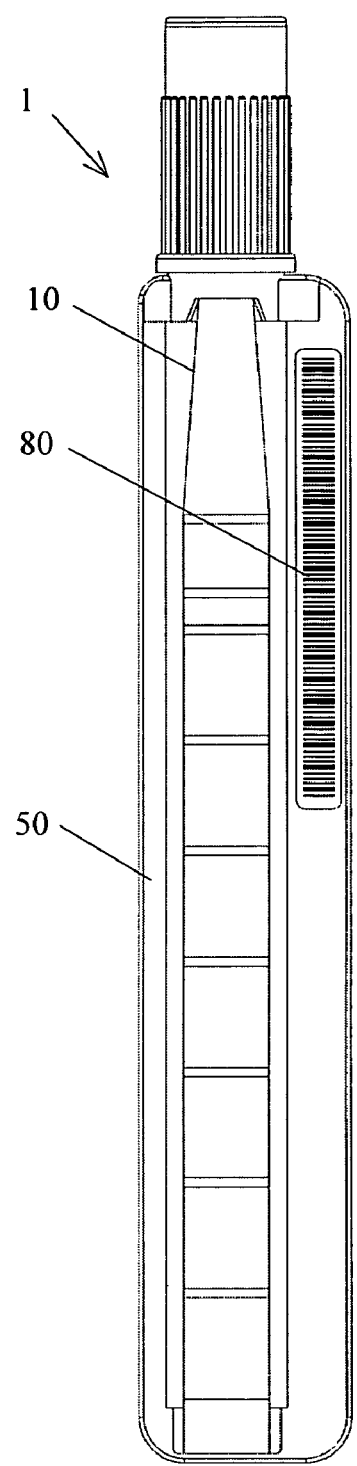
FIG. 1A is a front elevation view of an exemplary embodiment of a sample tube including a tubule.

The present disclosure describes devices and methods for processing samples. In several embodiments, segmented tubules provide a convenient vessel for receiving, storing, processing, and/or analyzing a biological sample. In certain embodiments, the segmented tubule facilitates sample processing protocols involving multiple processing steps. In certain embodiments, a sample may be collected in a sample tubule, and the tubule then positioned in an analyzer; the analyzer may then manipulate the tubule and its contents to process the sample.

A preferred embodiment includes a flexible tubule which has been segmented into compartments by breakable seals. The individual segments may contain various reagents and buffers for processing a sample. Clamps and actuators may be applied to the tubule in various combinations and with various timings to direct the movement of fluid and to cause the breakable seals to burst. This bursting of the breakable seals may leave an inner tubule surface that is substantially free of obstructions to fluid flow. In preferred embodiments, the flow of the biological sample may be directed toward the distal end of the tubule as the processing progresses, while the flow of waste may be forced to move in the opposite direction, toward the opening of the tubule where the sample was initially input. This sample inlet can be sealed, possibly permanently, by a cap with a locking mechanism, and a waste chamber may be located in the cap to receive the waste for storage. A significant benefit of this approach is that the processed sample does not come into contact with surfaces that have been touched by the unprocessed sample. Consequently, trace amounts of reaction inhibitors present in the unprocessed sample that might coat the walls of the tubule are less likely to contaminate the processed sample.

In some embodiments the tubule may be so expandable as to be capable of receiving a volume of fluid from each of multiple segments in one segment; this can allow sample and reagents to undergo certain processing steps in one segment leading to a simpler mechanical structure for performing assays. Another benefit of an embodiment using a tubule that may be so expandable is that the same tubule structure may be used to package different volumes of reagents within segments, allowing the same tubule to be packaged in differing ways depending upon the assay to be performed.

The apparatus may include a transparent flexible tubule 10 (FIGS. 1A-B, FIGS. 2A-B, and FIGS. 3A-B) capable of being configured into a plurality of segments, such as 16, 110, 120, 130, 140, 150, 160, 170, 180, and/or 190, and being substantially flattened by compression. In an embodiment, a tubule may have at least two segments. In an embodiment, a tubule may have at least three segments. The flexible tubule can provide operational functionality between approximately 2° C. and 105° C., compatibility with samples, targets and reagents, low gas permeability, minimal fluorescence properties, and/or resilience during repeated compression and flexure cycles. The tubule may be made of a variety of materials, examples of which include but are not limited to: polyolefins such as polypropylene or polyethylene, polyurethane, polyolefin co-polymers and/or other materials providing suitable characteristics. The tubule properties, such as transparency, wetting properties, surface smoothness, surface charge and thermal resilience, may affect the performance of the tubule. These proprieties may be improved through such exemplary processes as: seeding, plasma treating, addition of additives, and irradiation. In some embodiments, an additive material may be added to the plastic to improve selected characteristics. For example, a slip additive may be added, such as erucamide and/or oleamide; in some embodiment, a so-called "anti-block" additive may be added. An additive may have a concentration in the plastic in the range from about 0.01% to about 5.0%.

The tubule may be manufactured by a wide variety of suitable methods such as extrusion, injection-molding and blow-molding. In a preferred embodiment the tubule is continuously extruded. Alternative techniques for manufacturing the tubule include, e.g., casting, extruding or blowing films that can be fashioned by secondary processing operations into a suitable tubule. The tubule wall material may include multiple layers by co-extrusion, or by film lamination. For example, an inner layer may be chosen for high biocompatibility and an exterior layer may be chosen for low gas permeability. As a further example, the interior layer may be readily formed into a breakable seal 14 (FIG. 2A-B and FIGS. 3A-B), such as a peelable seal, while the exterior layer may be resilient and highly impermeable. For use in the present disclosure it is preferred the tubule have a wall thickness of about 0.03 mm to about 0.8 mm, preferably 0.03 mm to about 0.5 mm, with the tubule able to be substantially flattened with an applied exterior pressure on the order of 1 atmosphere.

Figure 7A:
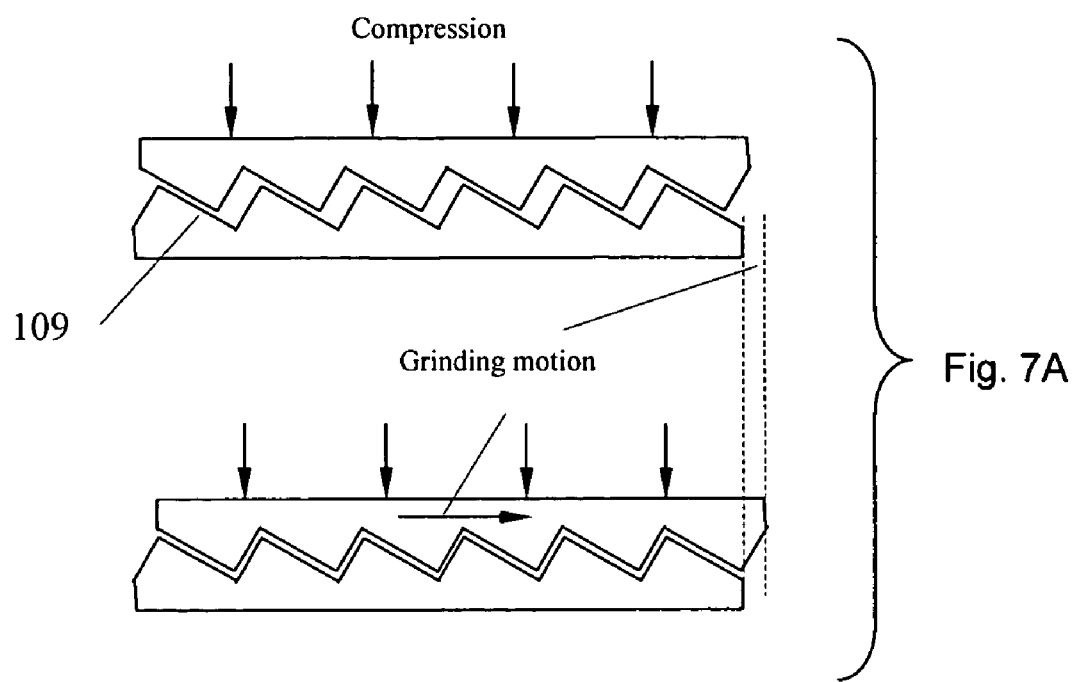
FIGS. 7A-B are, respectively, cross sectional and perspective views of exemplary embodiments of grinding systems.
Figure 7B:
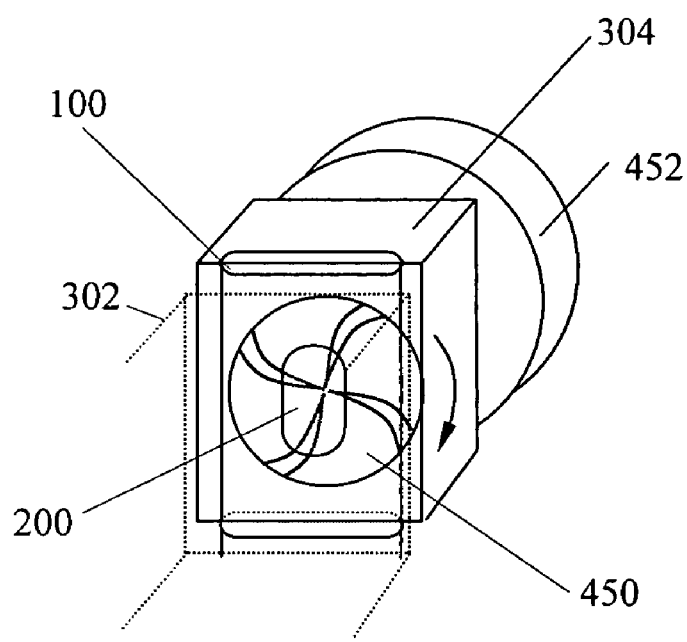

In some embodiments, the apparatus may have toughened walls in at least one segment to allow for the dislocation of clumps of cells from solid sample such as biopsy samples or solid environmental samples using grinding motions. An example of these toughened wall features, as illustrated in FIG. 7A, can be micro-teeth-like inner surfaces 109 on opposing faces of the tubule wall, which are offset such that compressing the tubule produces a sliding motion along the axis of the tubule. The tubule wall in the vicinity of these grinding surfaces 109 may be fortified using reinforcement patches made of a suitably resilient plastic such as polycarbonate or polyethylene terephthalate. The teeth-like inner surfaces may be made of similarly suitable materials. In another embodiment, a pad, such as 214 illustrated in FIGS. 5A-B, having grinding surface feature can be attached on the inner wall of tubule. The pad can be made by toughened material, and the surface feature can be created by using conventional mechanical, electrochemical or microelectromechanical methods, so that the pad can endure compression.

The sample tubule 10 may be partitioned into one or more segments 16, 110, 120, 130, 140, 150, 160, 170, 180, and/or 190, and/or sub-segments 18, 121, 122. In preferred embodiments, the segments are defined by breakable seals 14 to fluidly isolate adjacent segments. This seal feature can be useful in separating, for example, a dry reagent from a liquid reagent until the two can be reconstituted to perform a specific assay, or for separating chemically reactive species until the reaction is desired. As illustrated in FIGS. 3A-B, a breakable seal 14 may be formed in a region of the tubule 10 where opposing walls have been substantially joined, but not joined so strongly as to prevent the walls from being later peeled apart without significantly marring the tubule or the previously sealed surfaces. Such a seal may be termed a "peelable" seal. In a preferred embodiment, the peelable seal region may be a band orthogonal to the axis of the tubule. It may span a tubule length in the range of about 0.5 mm to 5 mm, preferably about 1 mm to about 3 mm, most preferably about 1 mm. The seal preferably spans the entire width of the tubule so as to seal the segment. In some embodiments, the seal band may vary in height or shape and/or be oriented at an angle transverse to the axis of the tubule; such variations can change the peel characteristics.

Breakable seals 14 can be created between opposing walls of the tubule by applying a controlled amount of energy to the tubule in the location where the peelable seal is desired. For example, a temperature controlled sealing head can press the tubule at a specific pressure against a fixed anvil for a specific time interval. Various combinations of temperature, pressure and time may be selected to form a seal of desired size and peel-strength. Energy may be delivered, for example, by a temperature controlled sealing head maintained at a constant temperature between 105° C. and 140° C. to heat a polypropylene tubing material; an actuator capable of delivering a precise pressure between 3 and 100 atmosphere over the desired seal region; and a control system to drive the sequencing of the actuator to a specific cycle time between 1 and 30 seconds. Using this method, satisfactory seals have been created in polypropylene tubules to peel open when subjected to an internal pressure on the order of 1 atmosphere. Alternate techniques to deliver the sealing energy to the tubule include RF and ultrasonic welding.

In other embodiments, alternate tubule materials and blends of materials can be used to optimize peelable seal performance. For example, two polypropylene polymers of differing melting temperature can be blended in a ratio such that the composition and melt characteristics are optimized for peelable seal formation. In addition to or in lieu of breakable seals 14, the flexible tubule can further have one or more pressure gates 194, which are capable of reversibly opening and closing during the operation of a test by applying a controlled force to a segment of the flexible tubule.

Figure 5A:
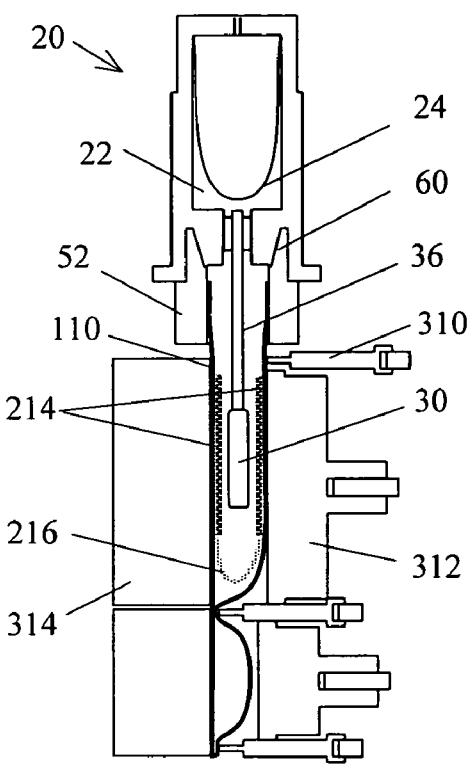
FIGS. 5A-B are, respectively, cross sectional and perspective views of exemplary embodiments of sample tubes positioned in analyzers.
Figure 5B:
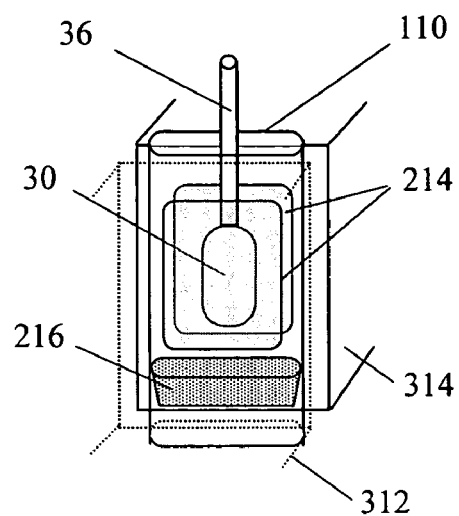
Figure 6A:
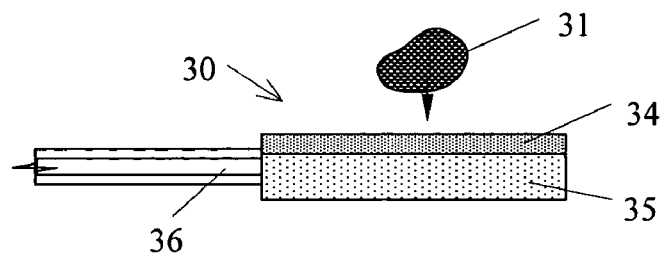
FIGS. 6A-C are cross sectional views of an embodiment of a sample collection device receiving a sample.
Figure 6B:
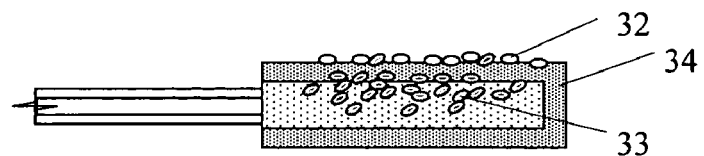
Figure 6C:
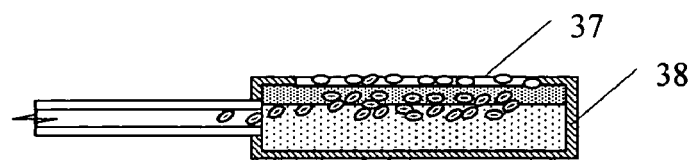

A filter can be embedded in a tubule segment. Examples of filters 206 and 216 are shown in FIG. 4A and FIGS. 5A-B, respectively, In a preferred embodiment, a filter can be formed by stacking multiple layers of flexible filter material. The uppermost layer of the filter that directly contacts a sample may have a pore size selected for filtration; the bottom layer of the filter may include a material with much larger pore size to provide a support structure for the uppermost layer when a pressure is applied during filtration. In this preferred embodiment, the filter may be folded to form a bag, with the edges of its open end firmly attached to the tubule wall. The segment with the filter bag may be capable of being substantially flattened by compressing the exterior of the tubule.

In exemplary embodiments, one or more reagents can be stored either as dry substance and/or as liquid solutions in tubule segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. In embodiments where one of the reagents is a chaotropic salt solution, a preferred component is guanidinium isocyanate or guanidinium hydrochloride or a combination thereof. In some embodiments, the order in which reagents may be stored in the tubule relative to the opening through which a sample is input, reflects the order in which the reagents can be used in methods utilizing the tube. In preferred embodiments, a reagent includes a substance capable of specific binding to a preselected component of a sample. For example, a substance may specifically bind to nucleic acid, or a nucleic acid probe may specifically bind to nucleic acids having particular base sequences.

In other exemplary embodiments, a solid phase substrate can be contained within a tubule segment and used to capture one or more selected components of a sample (if such component is present in a sample), such as a target microorganism or nucleic acids. Capturing can help to enrich the target component and to remove reaction inhibitors from a sample. Substrates may be solid phase material which can capture target cells, virions, nucleic acids, or other selected components under defined chemical and temperature conditions, and may release the components under different chemical and temperature conditions.

In some embodiments, a reagent can be coated on the substrate. Examples of coatable reagent are: receptors, ligands, antibodies, antigens, nucleic acid probes, peptide nucleic acid probes, phosphothioate nucleic acid probes, bacteriophages, silica, chaotropic salts, proteinases, DNases, RNases, DNase inhibitors, RNase inhibitors, and germinant solutions. In some embodiments, the substrate can be stored in a dry segment of the tubule while in other embodiments it can be stored immersed in a liquid. In some embodiments, the order in which reagents may be stored in the tubule relative to the substrate and the opening through which a sample is input, reflects the order in which the reagents and the substrate can be used in methods utilizing the apparatus.

The substrate can be: beads, pads, filters, sheets, and/or a portion of tubule wall surface or a collection tool. In embodiments where the substrate is a plurality of beads, said beads can be: silica beads, magnetic beads, silica magnetic beads, glass beads, nitrocellulose colloid beads, and magnetized nitrocellulose colloid beads. In some embodiments where the beads can be paramagnetic, the beads can be captured by a magnetic field. Examples of reagents that may permit the selective adsorption of nucleic acid molecules to a functional group-coated surface are described, for example, in U.S. Pat. Nos. 5,705,628; 5,898,071; and 6,534,262, hereby incorporated herein by reference. Separation can be accomplished by manipulating the ionic strength and polyalkylene glycol concentration of the solution to selectively precipitate, and reversibly adsorb, the nucleic acids to a solid phase surface.

When these solid phase surfaces are paramagnetic microparticles, the magnetic beads, to which the target nucleic acid molecules have been adsorbed, can be washed under conditions that retain the nucleic acids but not other molecules. The nucleic acid molecules isolated through this process are suitable for: capillary electrophoresis, nucleotide sequencing, reverse transcription, cloning, transfection, transduction, microinjection of mammalian cells, gene therapy protocols, the in vitro synthesis of RNA probes, cDNA library construction, and the polymerase chain reaction (PCR) amplification. Several companies offer magnetic-based purification systems, such as QIAGEN's MagAttract™, Cortex Biochem's MagaZorb™, Roche Applied Science's MagNA Pure LC™, and MagPrep® Silica from Merck & Co. All of these kits use negatively charged particles and manipulate buffer conditions to selectively bind a variety of nucleic acids to the beads, wash the beads and elute the beads in aqueous buffers. Many of the products used by these companies use chaotropic salts to aid in the precipitation of nucleic acids onto the magnetic beads. Examples are described in U.S. Pat. Nos. 4,427,580; 4,483,920; and 5,234,809, hereby incorporated herein by reference.

In some embodiments the substrate may be a pad 214 or 30 (FIGS. 5A-B, FIGS. 6A-C). In further embodiments, the substrate pad can include paper 35, alternating layers of papers 34 with different hydrophobic properties, glass fiber filters, or polycarbonate filters with defined pore sizes. In some embodiments, the pad may be a filter or impermeable sheet 38 for covering selected portion of the surfaces of the pad, said filter having a predetermined pore size. Such a filtration device can be used for separations of white blood cells 32 and red blood cells 33 (or other particles, such as virus or microorganisms) from whole blood 31 and/or other samples. The pad 214 can be mounted on the tubule wall (FIGS. 5A-B) and/or on a sample collection tool 26. In some embodiments the pad can be soaked with a reagent solution while in other embodiments it may be coated with dry reagents.

Figure 1B:
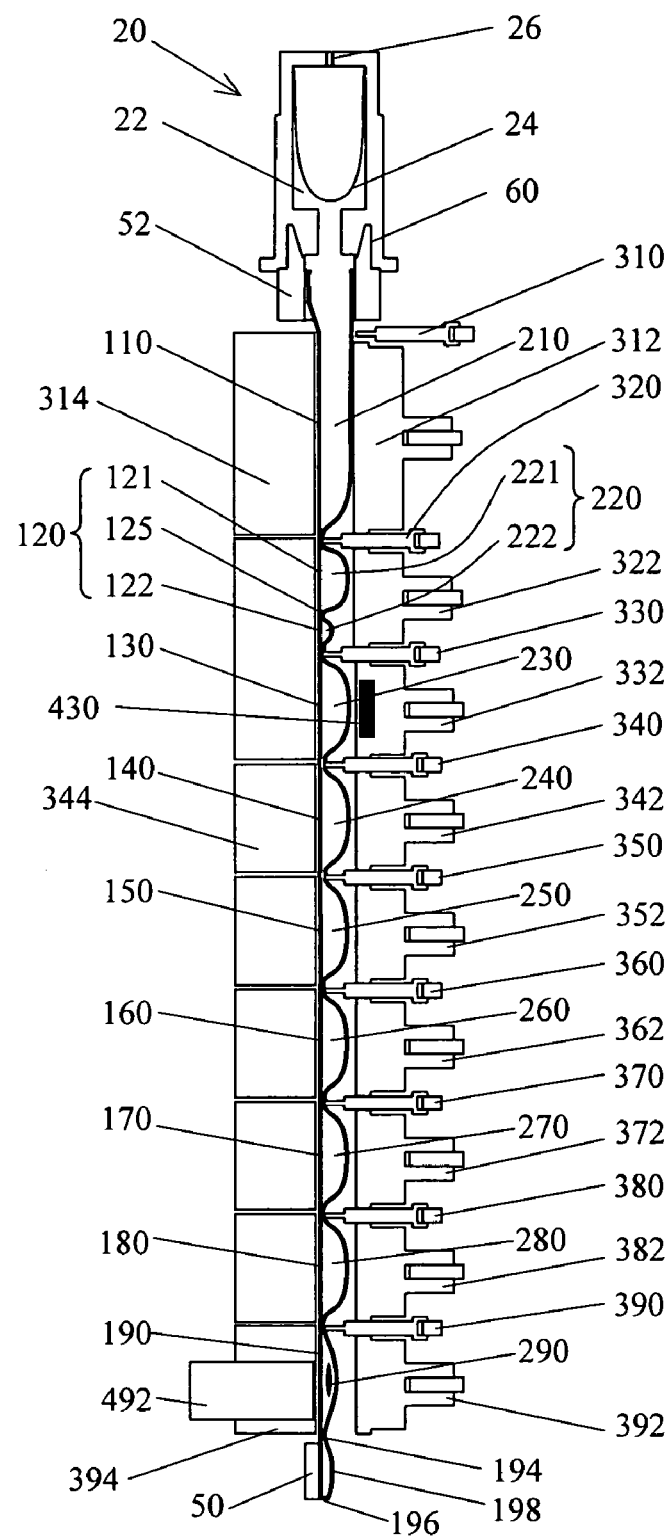
FIG. 1B is a cross sectional view of a sample tube positioned inside an analyzer.
Figure 2A:
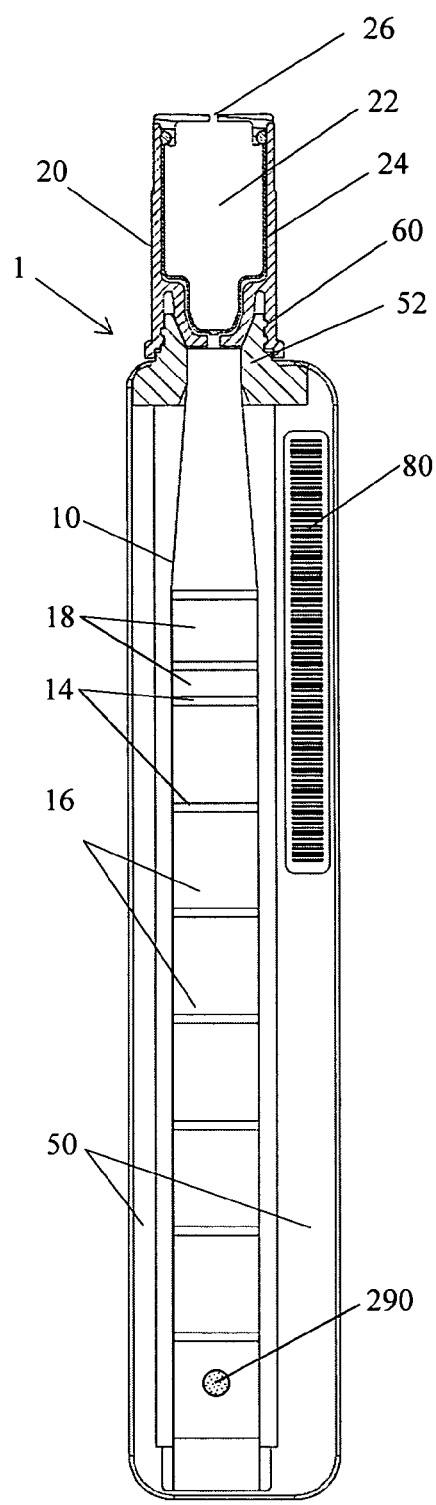
FIG. 2A is a cross sectional view of a sample tube including a tubule.
Figure 2B:
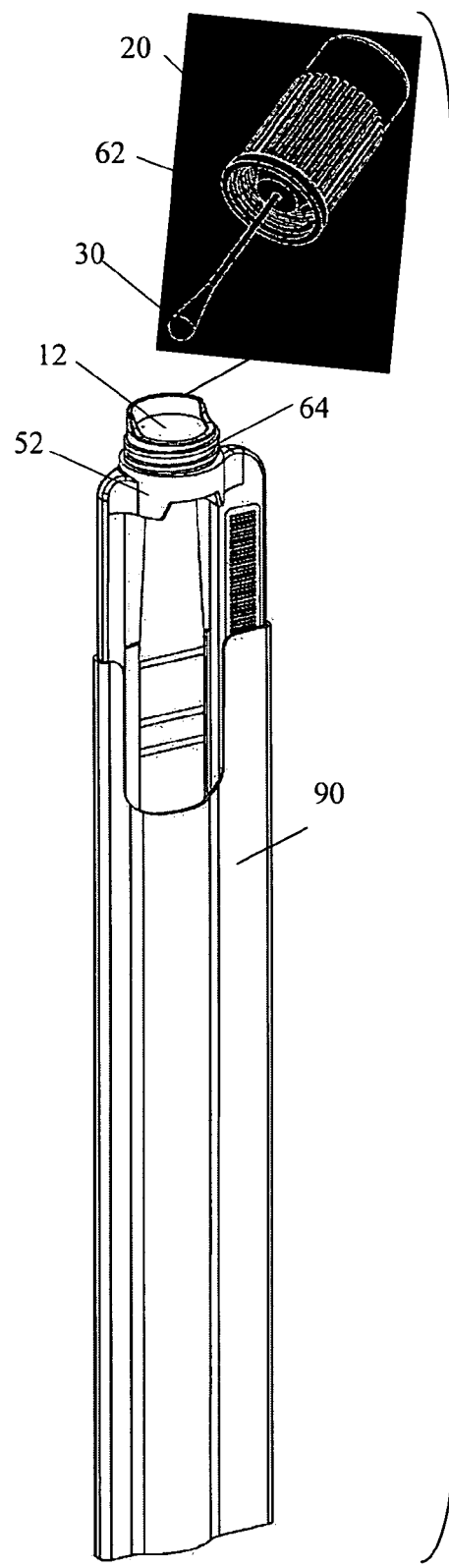
FIG. 2B is a perspective view of another exemplary embodiment of a sample tube.

Preferred exemplary embodiments may include a linear arrangement of 2 or more tubule segments 110, 120, 130, 140, 150, 160, 170, 180, and/or 190 (FIG. 1B). A linear arrangement facilitates moving the sample and resultant waste and target through the tube in a controlled manner. A raw biological sample can be input through a first opening 12 (FIG. 2B) in a first segment 110 (FIG. 1B) of the tubule. Thereafter, waste from a processed sample can be moved back toward the first opening while the target is pushed towards the opposite end, thereby minimizing contamination of the target by reaction inhibitors that may have become attached to the tubule wall, and confining the target to a clean segment of the tubule which can contain suitable reagents for further operations of the target. Some embodiments may use a plurality of at least three segments, each containing at least one reagent. In some embodiments, these segments may contain reagents in the following order: the reagent in the second segment may be either a lysis reagent, a dilution or wash buffer, or a substrate; the reagent in the third segment may be either a substrate, a lysis reagent, a washing buffer or a neutralization reagent; the reagent in the fourth segment may be a wash buffer, a suspension buffer, an elution reagent, or nucleic acid amplification and detection reagents. In some embodiments, the three segments may be arranged continuously, while in other embodiments, these three segments may be separated by another segment or segments in between.

In some embodiments, a pressure gate 194 can be incorporated to selectively close and open a second opening, located at the distal end of the tubule, to collect the products generated during a test from the tubule for further processing, outside of the tubule. In some embodiments, this second opening may located in a segment 198 defined by two pressure gates 194 and 196 to store a product from the sample processing segments. In some embodiments, a combination of a breakable seal and a pressure gate may be provided for transferring the contents of the tubule to a second opening.

In some embodiments a tube closing device for closing the tube after sample input may include a cap 20 (FIG. 1B) and/or clamp 310. An interface or adaptor 52 between the cap and the first opening of the flexible tubule may be used to ensure a secure, hermetic seal. In an exemplary embodiment, this interface may be threaded and may include tapered features 62 on the cap and/or a suitably rigid tube frame 50 such that, when fastened together, the threads 64 can engage to mate the tapered features 62 between the tube frame and cap to provide a suitable lock. In this exemplary embodiment the cap may require ½ to 1 full rotation to fully remove or attach from the tube holder. The combination of thread pitch and taper angle in the joint can be selected to be both easily manufactured and to provide feedback resistance to inform the user that an effective seal has been created. In other embodiments the cap locking device may include snap fits, press fits, and/or other types of "twist and lock" mechanism between the cap and tube holder, and similar arrangements in which the cap is permanently attached to the tubule, such as by hinging or tethering the cap.

Both the cap 20 and tube frame 50 can be made of a suitable injection molded plastic such as polypropylene. The tube frame 50 can, in turn, be fastened to the flexible tube by a permanent, hermetic seal. The exterior portion of the cap may be covered with ridges or finger grips to facilitate its handling. Furthermore, the cap 20 may include an area for attaching a sample identification mark or label. As a further alternative, the cap may be directly attached to the first opening flexible tube through a press fit or a collar that compresses the flexible tube opening against a protrusion in the cap to create a hermetic seal. The lock between the tube cap and tube holder may be keyed or guided such that a collection tool 36 or features integrated into the cap can be definitively oriented with respect to the tube to facilitate sample processing and the flattening of the flexible tubule. Furthermore, the cap may incorporate features such as a ratchet or similar safety mechanism to prevent the cap from being removed after it has been installed onto the opening of the flexible tube.

The cap 20 used to close the tubule in some embodiments may contain a cavity 22 within it by making the cap body substantially hollow. In some embodiments, the hollow portion extends from the top of the cap body to an orifice at the base of the cap body. To form a chamber, the top of the cavity may be closed by fastening a cover onto the cap body. The cover may be constructed of the same piece as the cap body. The cover may incorporate a vent hole 26 or may further incorporate an affixed microbe barrier, filter or a material that expands to close off the vent hole when exposed to a liquid or specific temperature. The bottom of the chamber may be left open or closed by a breakable septum or valve. The hollow chamber may further incorporate a flexible membrane or septum 24. This flexible septum could be manufactured using dip molding, liquid injection silicone molding, blow molding, and/or other methods suitable for the creation of thin elastomeric structures. The flexible septum can be inserted into the cap body cavity 22 assembly so as to effectively isolate the interior portion of the tube from the exterior environment after the cap is in place on the tube. The flexible septum could be designed such that, in the absence of externally applied pressures, its inherent stiffness ensures it is in a preferred, known state of deformation. As a further embodiment, the flexible septum may be replaced by a plunger. In an exemplary embodiment, a cap body approximately 30 mm high by 14 mm diameter may be injection molded of a suitable thermoplastic and contain an interior cavity having at least 500 µL of available volume. The chamber in the cap body could be adapted for useful purposes such as holding or dispensing a reagent, serving as a reservoir to hold waste fluids, serving as a retraction space for an integrated collection tool, or a combination of thereof.

The cap 20 may have an integrated collection tool 30 (FIG. 2B) such as a swab, capillary tube, liquid dropper, inoculation loop, syringe, absorbent pad, forceps, scoop or stick to facilitate the collection of liquid and solid samples and their insertion into the tubule. The collection tool may be designed to collect and deposit a predetermined amount of material into the tube. Reagents may be stored on the collection tool itself. For example, the collection tool may include a swab impregnated with a dry salt such that when the swab is hydrated it would suspend the salt off the swab into solution. Furthermore, the collection tool and cap may be designed such that the collection tool portion retracts into the cap body after depositing the sample into the tubule to leave the tubule segments substantially unencumbered.

The chamber 22 in the cap may be fashioned to store a reagent. To accomplish this, for example, the base of the chamber may be closed by a breakable septum or valve (not shown) such that when the cap is squeezed, the septum breaks to release the reagent. Such a feature would be useful, for example, if the cap were integrally formed with a collection tool such as a swab or stick. In this instance, the reagent released from the cap chamber could be used to wash a sample off the collection tool into a tube segment or to lyse the sample contained on the collection tool. Reagents may also be released from the cap chamber by opening the breakable septum using pressure generated by compressing a flexible tube segment to force fluid from the tube up into the cap chamber. The chamber in the cap may be fashioned to store waste fluids derived from processing within the tubule. In a preferred embodiment, the base of the chamber may be left open such that when connected to the first opening of the flexible tubule a fluid passage is formed between the tubule and the chamber. As fluid is moved into the cap chamber, the flexible septum 24 contained within can move from an initial position upward so as to accommodate the influx of new fluid. This septum movement can be facilitated by the incorporation of a vent hole 26 on the cap body cover.

After fluid has been transferred into the cap chamber a clamp 310 or actuator 312 can act to compress the tubule and effectively seal off the cap chamber volume from the tubule segments. As an alternative embodiment, the cap chamber may incorporate a pressure gate or check valve (not shown) to prohibit fluid flow from the cap chamber back into the tube segments. As a further alternative, the flexible septum may be omitted with the cap chamber cover including a microbe barrier to permit the free escape of contained gasses but retain all the liquid volumes and infectious agents in the tube. As a further alternative, the flexible septum can be replaced with a plunger that would move axially upward to accommodate additional fluid volumes transferred from the tube segments to the cap chamber. Other methods to accommodate fluidic waste within the cap chamber can be readily envisioned without departing from the scope of the present disclosure.

A substantially rigid frame 50 may be provided to hold the flexible tubule 10 suitably taut by constraining at least the proximal and distal ends of the tubule. In an exemplary embodiment, a first constraint may be provided to permanently attach and seal the tubule to the frame around the first opening of the tube. This seal may be created by welding the flexible tubule to the frame using thermal and/or ultrasonic sources. Alternatively, the seal may be created using a hot-melt adhesive joint with ethylene vinyl acetate, or by making a joint using a UV cure epoxy or other adhesives. In further embodiments, the tubule may be mechanically sealed or insert-molded with the frame. A second constraint may be provided to attach and seal the tubule to the base of the frame. In an exemplary embodiment of this second constraint, this end of the tubule may be sealed flat and attached to the rigid frame by thermal and/or ultrasonic welding techniques. Alternatively, this joint and seal may also be formed using adhesive or mechanical approaches. In an alternative embodiment, the second seal may be similar to the first seal, being substantially open to enable access to the contents of the flexible tubule from the second opening. The tubule and frame materials can be optimized for joint manufacture. For example, the frame can be made of polypropylene having a lower melting point than the thinner tubule to ensure more uniform melting across one or more weld zones. To facilitate welding between the tubule and the frame, the joint area may be tapered or otherwise shaped to include energy directors or other commonly used features enhance weld performance. In an exemplary embodiment, the rigid frame can be made of any suitable plastic by injection molding with its dimensions being approximately 150 mm tall by 25 mm wide.

The rigid frame 50 can incorporate several features to facilitate the compression and flattening of the flexible tubule. For example, in an exemplary embodiment, the flexible tubule 10 may be constrained only at its two axial extremities to allow maximum radial freedom to avoid encumbering the tubule's radial movement as it is compressed. In another embodiment, compression may be facilitated by including a relief area in the frame, near the first opening of the tube. This relief area may be used to facilitate the flexible tubule's transition from a substantially compressed shape in the tubule segments to a substantially open shape at the first opening. Other useful features of the rigid frame that can facilitate flexible tubule compression may include an integral tubule tensioning mechanism. In an exemplary embodiment, this tension mechanism could be manufactured by molding features such as cantilever or leaf type springs directly into the rigid frame to pull the tubule taut at one of its attachment points with the frame.

The rigid frame 50 can facilitate tube identification, handling, sample loading and interfacing to the tube cap. For example, the frame can provide additional area to identify the tube through labels or writing 80 affixed thereto. The plastic materials of the frame may be color coded with the cap materials to help identify the apparatus and its function. The frame may incorporate special features such as changes in thickness or keys to guide its orientation into a receiving instrument or during manufacture. The frame may interface to a sleeve 90 or packaging that covers or protects the flexible tubule from accidental handling damage, light exposure, and/or heat exposure. The body of the rigid frame may also provide a convenient structure to hold the tube. The frame may have an integral collection tool 32 such as a deflector or scoop to facilitate sample collection into the apparatus. The sample-receiving end of the frame may also incorporate a tapered or funneled interior surface to guide collected sample into the flexible tube.

In some embodiments, a method of extracting nucleic acids from biological samples by using the apparatus described in the previous paragraphs is contemplated. In certain embodiments, the sequence of events in such a test may include: 1) a biological sample collected with a collection tool, 2) a flexible tubule, which can include a plurality of segments that may contain the reagents required during the test, and in which the collected sample can be placed using a first opening in the tubule, 3) at least one substrate that may be set at a controlled temperature and/or other conditions to capture target organisms or nucleic acids during a set incubation period, 4) organisms or molecules, in the unprocessed sample, that may not bind to the substrate and could thus be removed by transferring liquid to a waste reservoir, 5) storing waste, in a waste reservoir, that can be segregated from the target by a clamp and/or actuator compressed against the tubule, 6) a wash buffer, released from another segment of the tubule, that can remove reaction inhibitors, 7) an elution reagent, from another segment, that can release the target bound to the substrate after incubation at a controlled temperature, and 8) nucleic acids that can be detected by techniques well known to those familiar in the art or collected through a second opening in the tubule. In exemplary embodiments the flow of the sample may be from the first opening towards the distal end of the tubule as the test progresses while the flow of waste may be towards the closed sample input opening of the tubule, where a waste chamber in the cap of the tubule receives the waste for storage. Consequently, undesirable contact between a processed sample and surfaces in a reaction vessel that have been touched by the unprocessed sample is avoided, thereby preventing reaction inhibition due to trace amounts of reaction inhibitors present in the unprocessed sample and that might coat the walls of the reaction vessel.

Some embodiments may incorporate the use of a test tube 1, with a flexible tubule 10 divided into a plurality of segments, such as segments 16, 110, 120, 130, 140, 150, 160, 170, 180, and/or 190, that may be transverse to the longitudinal axis of the tubule, and which may contain reagents, such as reagents 210, 221, 222, 230, 240, 250, 260, 270, 280, and/or 290; as well as an analyzer, that may have a plurality of actuators, such as actuators 312, 322, 332, 342, 352, 362, 372, 382, and/or 392, clamps, such as clamps 310, 320, 330, 340, 350, 360, 370, 380, and/or 390, and blocks, for example 314, 344, and/or 394 (others unnumbered for simplicity); opposing the actuators and clamps, to process a sample. Various combinations of these actuators, clamps, and/or blocks may be used to effectively clamp the tubule closed thereby segregating fluid. In exemplary embodiments, at least one of said actuators or blocks may have a thermal control element to control the temperature of a tubule segment for sample processing. The sample processing apparatus can further have at least one magnetic field source 430 capable of applying a magnetic field to a segment. The sample processing apparatus can further have a detection device 492, such as photometer or a CCD, to monitor a reaction taking place or completed within the tubule.

The combined use of the tube and the analyzer can enable many sample processing operations. Collecting a sample, such as blood, saliva, serum, soil, tissue biopsy, stool or other solid or liquid samples, can be accomplished by using a sample collection tool 30 that may be incorporated into the cap 20, or features 32 on the tube frame 50. After a suitable amount of the sample has been collected, the cap can be placed onto the first opening of the tube to close the tube and deposit the sample into the first segment. Following this step, the sample contained on the collection tool may be washed off or re-suspended with reagents contained in separate chambers within the cap by compressing a potion of the cap. The tube can then be loaded into the analyzer for further processing. Identification features, such as a barcode or an RF tag, can be present on the tube to designate the sample's identity in a format that can be read by the analyzer and/or a user.

Opening a breakable seal of a tubule segment can be accomplished by applying pressure to the flexible tubule to irreversibly separate the bound surfaces of the tubule wall. An actuator can be used to apply the required pressure to compress a tubule segments containing fluid to open a breakable seal. In embodiments where a segment is delimited by two breakable seals, A and B, the analyzer may preferentially break seal A by physically protecting the seal B region with an actuator or clamp to prevent seal B from breaking while pressure is applied to the segment to break seal A. Alternatively, seal A may be preferentially opened by applying pressure to the segment adjacent to seal A in a precise manner such that; seal A is first opened by the pressure created in the adjacent segment; after seal A is broken, the pressure between the two segments drops substantially due to the additional, combined, segment volume; the reduced pressure in the combined segment is insufficient to break seal B. This method can be used to open breakable seals one at a time without using a protecting actuator and/or clamp. As a further alternative, the adherence of seal A may be inferior to that of seal B such that seal A can break at a lower pressure than seal B.

A process of moving fluid from one segment to another segment may include, for example, releasing a clamp on one end of the first segment, compressing a clamp on the other end of the first segment, releasing an actuator on the second segment, and compressing an actuator on the first segment to move the liquid from the first segment to the second segment. Alternatively, the clamp may be omitted or be opened after releasing the actuator on the second segment.

A process of mixing two substances, where at least one is liquid, located in adjacent segments may be accomplished by: releasing the clamp between the two segments, moving the liquid contained in the first segment, through an opened breakable seal to the second segment; and alternatively compressing the second segment and the first segment to flow the liquid between the segments.

An agitation can be performed by alternatively compressing and decompressing a tubule segment with an actuator, while both clamps that flank the actuator are compressing the tubule. In another embodiment, agitation can be achieved by alternatively moving liquid between at least two segments.

In embodiments where a tubule segment may contain a liquid having a volume exceeding the volume required for a protocol, a process of adjusting the volume of the liquid in the segment can be executed by: compressing the tubule segment to reduce the gap of between the tube walls to set the volume of the segment to a desired level and allowing the exceeding liquid to flow to the adjacent segment, past a clamp at the end of the segment or adjacent actuator; closing the tubule segment with the clamp or actuator, resulting in an adjusted volume of liquid remaining in the segment.

A process of removing air bubbles may include agitating a segment containing the bubbly liquid. Another process of removing air bubbles may include agitating a first segment containing liquid while closing a second segment; opening the second segment and moving the liquid from the first segment to the second segment; agitating the second segment and adjusting a position of the second actuator to move the liquid-air interface near or above the upper end of the second segment, then clamping the upper end of the second segment to form a fully liquid-infused segment without air bubbles.

A dilution process can be conducted by using the liquid movement process wherein one of the segments includes a diluent and the other includes a substance to be diluted.

A process of reconstituting a reagent from dry and liquid components separately stored in different tubule segments or sub-segments may include compressing the tubule segment or sub-segment containing the liquid components to open the breakable seal connecting to the dry reagent segment, moving the liquid into the dry reagent segment or sub-segment, and mixing the dry reagent and liquid components using the mixing process.

Filtration can be performed by using a filter 206 (FIG. 4A) positioned between two segments or two sub-segments. For example, a whole blood sample can be deposited into a first segment with a filter bag. A pore size of the filter can be selected for blood cell filtration. A clamp 300 can then close the end of the segment opposite to the filter bag, and an actuator 302 can compress the first segment to generate pressure to drive plasma flow through the filter into a second segment. In another embodiment, a coagulation, aggregation or agglutination reagent, such as antibody 204 against red cell 202 surface antigens, a red cell coagulate, can be used to induce red cell-red cell binding to form clusters prior to the filtration. The pore size of the filter can be selected to block the clusters while allowing non-aggregated cells to flow through. Applying pressure on the first segment containing red cell clusters and blood can enrich the white cells 208 in the second segment.

In some embodiments, a grinding process can be conducted by using an actuator to alternately compress and decompress a tubule segment having a toughened wall with a micro-teeth-like inner surface 109 (FIG. 7A), and thus breakup a solid sample, such as biopsy tissue sample, within the tubule segment. In another embodiment, small glass beads can be used with the solid sample to improve the performance of grinding. In a further embodiment, a grinding wheel 450 driven by a motor 452 can be used to form a rotational grinding onto the sample in the tubule segment and drive the movement of glass beads and a biological sample 200 to improve grinding performance. The temperature of a liquid reactant in the segment can be selected so as to improve the grinding result.

Incubation of the contents in a segment can be achieved by setting the corresponding actuator and/or block temperature and applying pressure to the segment to ensure a sufficient surface contact between the tubule wall of the segment and the actuator and the block, and bring the contents of the tubule segment to substantially the same temperature as the surrounding actuator and/or block temperature. The incubation can be conducted in all processing conditions as long as the temperatures of all involved segments are set as required.

Rapid temperature ramping for incubation can be achieved by incubating a fluid in a first segment at a first temperature and setting a second temperature for a second segment adjoining the first segment, after incubation at the first temperature is finished, liquid is rapidly moved from the first segment to the second segment and incubated at the second temperature.

A flow driving through a flow-channel process can be performed by compressing the tubule with a centrally-positioned actuator, and its flanking clamps if any, to form a thin-layer flow channel with a gap of about 1 to about 500 µm, preferably about 5 to about 500 µm through segment. The adjacent actuators compress gently on the adjacent segments in liquid communication with the flow-channel to generate an offset inner pressure to ensure a substantially uniform gap of the thin-layer flow channel. The two flanking actuators can then alternatively compress and release pressure on the tubule on their respective segments to generate flow at controlled flow rate. Optional flow, pressure, and/or force sensors may be incorporated to enable closed-loop control of the flow behavior. The flow-channel process can be used in washing, enhancing the substrate binding efficiency, and detection.

A magnetic bead immobilization and re-suspension process can be used to separate the beads from the sample liquid. The magnetic field generated by a magnetic source 430 (FIG. 1B) may be applied to a segment 130 containing a magnetic bead suspension 230 to capture and immobilize the beads to the tube wall. An agitation process can be used during the capturing process. In another embodiment, a flow-channel can be formed on the segment with the applied magnetic field, and magnetic beads can be captured under flow to increase the capturing efficiency. For re-suspending immobilized beads, the magnetic field may be turned off or removed, and an agitation or flow-channel process can be used for re-suspension.

A washing process to remove residual debris and reaction inhibitors from a substrate may be conducted by using three basic steps: First an actuator can compress a segment containing the substrate, such as immobilized beads or a sheet, to substantially remove the liquid from this segment. Second, a washing buffer may be moved to the segment by using a process similar to that of reconstituting a reagent from dry and liquid components. For bead-based substrates, a bead re-suspension process can be used followed by bead re-capture on the tubule wall. Third, after a mixing or agitation process, the actuator can compress the segment to remove the used wash liquid from the segment. In another embodiment, a flow-channel can be formed in the segment containing a substrate, which may be either immobilized beads or a sheet. A unidirectional flow wash, having laminar characteristics, is generated through the flow channel with the substrate. Finally, all the actuators and clamps, if any, can be closed to remove substantially all the liquid from the segments. In a further embodiment, a combination of the dilution based washing and the laminar flow based washing can be used to further enhance the washing efficiency.

Lysis can be achieved by heating a sample at a set temperature or by using a combination of heat and chemical agents to break open cell membranes, cell walls or uncoat virus particles. In another embodiment, lysis can be achieved using a chemical reagent, such as proteinase K, and a chaotropic salt solution. Said chemical reagents can be stored in one of more tubule segments and combined with the sample using the processes disclosed above. In some embodiments, multiple processes such as chemical cell lysis, mechanical grinding and heating, can be combined to break up solid sample, for example tissue collected from biopsy, to maximize the performance.

Capturing target micro-organisms can be achieved by using a substrate. In an embodiment, the surface of the substrate may be coated with at least one binding reagent, such as an antibody, ligand or receptor against an antigen, receptor or ligand on the surface of the target organism (ASA), a nucleic acid (NA), a peptide nucleic acid (PNA) and phosphothioate (PT) nucleic acid probe to capture a specific nucleic acid target sequence complementary to the probe or a target organism. In another embodiment, the surface may be selected to have, or coated to form, an electrostatically charged (EC) surface, such as silica- or ion exchange resin-coated surface, to reversibly capture substantially only nucleic acids. In some embodiments, the substrate may be pre-packed in a tubule segment or sub-segment in dry format, and a liquid binding buffer may be packed in another segment. The substrate and the buffer can be reconstituted by using the aforementioned processes.

In some embodiments, a reagent from an adjoining segment can be used to dilute the sample before incubation with the substrate. In some embodiments, the target organisms can be captured to the substrate prior to lysing the microorganisms; while in other embodiments, a lysis step can be conducted before the target capturing step. In preferred embodiments, incubation of the substrate in agitation can be conducted at a desired temperature, for example, at 4° C. for live bacterial capture, or room temperature for viral capture. Capture can be followed by a washing process to remove the residues and unwanted components of the sample from the tubule segment.

In some embodiments, magnetic beads can be used as the substrate for capturing target, and a magnetic bead immobilization and re-suspension process may be used to separate the beads from the sample liquid. In other embodiments where the substrate may be a pad 30 or a sheet 214 (FIGS. 5A-B), the substrate 30 and 214 may be incorporated into the collection tool 36 and/or may be adhered on the tubule wall in a segment.

Elution can be achieved by heating and/or incubating the substrate in a solution in a tubule segment at an elevated temperature. Preferred temperatures for elution are from 50° C. to 95° C. In another embodiment, elution may be achieved by changing the pH of the solution in which the substrate is suspended or embedded. For example, in an exemplary embodiment the pH of the wash solution can be between 4 and 5.5 while that of the elution buffer can be between 8 and 9.

A spore germination process can be conducted by mixing a sample containing bacterial spores with germination solution, and incubating the mixture at a suitable condition. The germinant solution may contain at least one of L-alanine, inosine, L-phenylalanine, and/or L-proline as well as some rich growth media to allow for partial growth of the pre-vegetative cells released from the spores. Preferred incubation temperatures for germination range from 20° C. to 37° C. By coating the substrate with an anti-spore antibody, vegetative cells can be selectively enriched from a sample that contains both live and/or dead spores. The live spores can release a plurality of vegetative cells from the substrate, which can be further processed to detect nucleic acid sequences characteristic of the bacterial species. In some embodiments, the germinant solution can be absorbed in a pad.

In certain embodiments, nucleic acids extracted from the biological samples may be further processed by amplifying the nucleic acids using at least one method from the group: polymerase chain reaction (PCR), rolling circle amplification (RCA), ligase chain reaction (LCR), transcription mediated amplification (TMA), nucleic acid sequence based amplification (NASBA), and strand displacement amplification reaction (SDAR). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nickedcircular nucleic acid probes can be circularized using T4 DNA ligase or Ampligase™ and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., Taq-Man™, molecular beacons™, fluorescence resonance energy transfer (FRET) probes, scorpion™ probes) and generally use fluorescence quenching as well as the release of quenching or fluorescence energy transfer from one reporter to another to detect the synthesis or presence of specific nucleic acids.

A real-time detection of a signal from a tubule segment can be achieved by using a sensor 492 (FIG. 1B), such as a photometer, a spectrometer, a CCD, connected to a block, such as block 490. In exemplary embodiments, pressure can be applied by an actuator 392 on the tubule segment 190 to suitably define the tubule segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

The disclosed devices and methods can be widely applied in the practice of medicine, agriculture and environmental monitoring as well as many other biological sample testing applications. Nucleic acids isolated from tissue biopsy samples that surround tumors removed by a surgeon can be used to detect pre-cancerous tissues. In these applications, hot-spot mutations in tumor suppressor genes and proto-oncogenes can be detected using genotyping techniques well known to those familiar with the art. Precancerous tissues often have somatic mutations which can readily be identified by comparing the outcome of the genotyping test with the biopsy sample to the patient's genotype using whole blood as a source of nucleic acids. Nucleic acids isolated from white blood can be used to detect genetic variants and germline mutations using genotyping techniques well known to those familiar with the art. Examples of such mutations are the approximately 25 known mutants of the CFTR gene recommended for prenatal diagnosis by the American College of Medical Genetics and the American College of Obstetricians and Gynecologists. Examples of genetic variants are high frequency alleles in glucose-6-phosphate dehydrogenase that influence sensitivity to therapeutic agents, like the antimalarial drug Primaquine.

Another example of genetic variations with clinical relevance are alleles pertaining to increased risks of pathological conditions, like the Factor V Leiden allele and the increased risk of venous thrombosis. Nucleic acids isolated from bacteria can be used to detect gene coding sequences to evaluate the pathogenicity of a bacterial strain. Examples of such genes are the Lethal Factor, the Protective Antigen A, and the Edema factor genes on the PXO1 plasmid of *Bacillus anthracis* and the Capsular antigen A, B, and C on the PXO2 plasmid of the *B. anthracis*. The presence of these sequences allows researchers to distinguish between *B. anthracis* and harmless soil bacteria. Nucleic acids isolated from RNA viruses can be used to detect gene coding sequences to detect the presence or absence of a virus or to quantify a virus in order to guide therapeutic treatment of infected individuals.

A particularly significant utility of such assays is the detection of the human immunodeficiency virus (HIV), to guide anti-retroviral therapy. Nucleic acids isolated from DNA viruses can be used detect gene coding sequences to detect the presence or absence of a virus in blood prior to their use in the manufacturing of blood derived products. The detection of hepatitis B virus in pools of blood samples is a well-known example of this utility to those familiar in the art. The presence of verotoxin *Escherichia coli* in ground beef is a good example of the potential agricultural uses of the apparatus. Detecting the Norwalk virus on surfaces is an example of a public health environmental monitoring application.

EXAMPLES

Example 1

Genomic DNA Isolation and Detection from Whole Blood

DNA isolation and DNA sequence detection can be accomplished in a tube 1 (FIG. 1B), including a flexible tubule 10 having nine segments separated by peelable seals and containing pre-packed reagents, and a cap 20, having a waste reservoir 22 housed therein. The first segment 110 of the tubule can receive the whole blood sample. The second segment may contain dilution buffer having 40 µl of phosphate buffered saline (PBS) 221 (which may contain 137 mM NaCl, 2.7 mM KCl, 4.3 mM $Na_2HPO_4$, 1.4 mM $KH_2PO_4$, pH 7.3) and 250 µg dry proteinase K 222, which can be housed in sub-segment one 121 and two 122 respectively, separated by a peelable seal 125. The third segment 130 may contain 50 µl of lysis buffer 230 that may contain chaotropic salts which may contain 4.7 M guanidinium hydrochloride, 10 mM urea, 10 mM Tris HCl, pH 5.7, and 2% triton X-100. The fourth segment 140 may contain 500 µg of magnetic silica beads 240, such as MagPrep™ beads (Merck & Co), suspended in 80 µl of isopropanol. These beads can bind DNA in the presence of chaotropic salts and alcohol. The fifth segment 150 may contain 80 µl of wash buffer 250 (which may contain 50% ethanol, 20 mM NaCl, 10 mM Tris HCl, pH7.5). The sixth segment 160 may contain 80 µl of 20 mM 2-morpholinoethanesulfonic acid (MES) buffer 260, pH 5.3. The pH of the MES buffer may be adjusted such that it can be low enough to avoid DNA elution from the beads. The seventh segment 170 may contain 80 µl elution buffer 270 (10 mM Tris HCl, pH 8.5: an example of a buffer suitable for PCR). The pH of the elution buffer may be adjusted such that it can be high enough to elute the DNA from the surface of the beads into the buffer. The eighth segment 180 may contain dry uracil-N-glycosylase (UNG) 280. The ninth segment 190 may contain dried PCR reagents 290 (which may contain 10 nmol of each one of the 3 deoxynucleotide triphosphates (dNTPs): deoxyadenosine triphosphate (dATP), deoxycytosine triphosphate (dCTP), and deoxyguninosine triphosphate (dGTP); 20 nmol deoxyuridine triphosphate (dUTP), 2.5 µmol of KCl, 200 nmol of $MgCl_2$, 1-5 units of Taq DNA polymerase, and 20-100 pmol of each of the oligonucleotide primers, and 6-25 pmol of TaqMan probe). The end 194 of the segment 190, can be permanently sealed or contain a pressure gate for collecting the products of the amplification reaction to confirm the results of a genotyping test by DNA sequencing or some other test known to those skilled in the art.

For genotyping, over 10 µl of whole blood may be loaded into the first segment 110. The tubule can then be closed by a cap 20 and inserted into an analyzer. Sample processing may include the following steps.

1. Sample Lysis. All clamps, except the first clamp 310, may be closed on the tubule. The first actuator 312 may compress the first segment 110 to adjust the volume of blood 210 to retain about 10 µl in the segment, and then the first clamp 310 may compress the tubule to close the segment. The second actuator 322 can then compress the second segment 120 (subsegments 121 and 122) to break the peelable seal 125 and mix PBS 221 with proteinase K 222. The second clamp 320 can then open, and the second actuator can compress the second segment to open the peelable seal. The first and second actuators may further alternately compress the segments to mix the dilution buffer with the blood sample. The analyzer can close the first actuator 312 and second clamp 320 to move the diluted sample to the second segment 120, and move the third clamp 330 to open and actuator 322 and 332 to alternately compress the tubule segments 130 and 120 to open the peelable seal in-between the segments to mix the lysis buffer 230 with the diluted sample, and incubate the mixture at 50° C. for 5 minutes. The incubation temperature can be maintained by contact between the tubule and the thermal elements incorporated within the actuators and/or blocks opposing the actuators.

2. Nucleic Acid Capture. After incubation, the fourth clamp 340 can open and the fourth actuator 342 may compress the fourth segment 140 to open the peelable seal and mix the magnetic silica beads suspended in isopropanol 240 with the lysate in segments 130 and/or 120. The actuators 322 and 332 with an adjacent actuator 312 or 342 can alternately compress their respective segments to agitate and incubate the mixture for 5 minutes at room temperature to facilitate DNA binding to the magnetic silica beads. Then, a magnetic field can be generated by a magnetic source 430 near the segment 130 to capture the beads in suspension. The actuator 322 and 332 can alternately compress segment 120 and 130 to capture beads. As an alternative, the actuator 332 can compress segment 130 to form a flow-channel, and two flanking actuators 322 and 342 can compress their respective segments alternately to increase the capture efficiency. Substantially all the beads can be immobilized on the wall of segment 130, then the actuators and clamps from actuator 342 to clamp 310 can be sequentially opened and closed to move the unbound sample and waste to the waste reservoir 22.

3. Wash. A wash process can follow the capture process in order to remove residual debris and reaction inhibitors from the beads and the segments that would be used for further sample processing. In this embodiment, a dilution based washing can be used with the ethanol wash buffer and a thin-layer flow based washing can be used with the MES wash buffer. Clamps 350 and actuator 342 can first open, and then actuator 352 can close to move the ethanol buffer 250 to segment 240, followed by the closing of clamp 350. By using the same process on segments 140 and 130, the ethanol buffer can be moved to segment 130. The magnetic field can be removed; the actuator 332 and at least one adjacent actuator can be alternately compressed against their respective segments to generate flow to re-suspend the beads. The magnetic field can then be turned on to capture substantially all the beads and the liquid can be moved to waste reservoir by using the processes mentioned above. After completing the first wash, the MES wash buffer can be moved from segment 160 to 140. Actuator 332 and clamp 340 and 330 can be gently released to form a thin-layer flow channel through segment 130. Actuator 342 can compress gently on segment 140 to generate a certain inner pressure to ensure a substantially uniform gap of the thin-layer flow channel. Actuator 342 can then gently compress the tubule, and actuator 322 can release the tubule to ensure an essentially laminar flow of the wash buffer through the flow channel. When the wash is completed, the actuators and clamps can close and substantially all the waste may be moved to the waste reservoir 22.

4. Nucleic Acid Elution. The elution buffer 270 may then be moved from segment 170 to 130 by using a similar process as mentioned before. The magnetic field can be removed and the beads can be re-suspended in the elution buffer under flow between segments 130 and 140. The bead suspension can be incubated at 95° C. under stationary, flow or agitation conditions for 2 minutes. The magnetic field may be turned on and substantially all the beads can be immobilized, and the eluted nucleic acid solution can be moved to segment 170 by sequentially opening and closing the actuators and clamps. The actuator 372 can compress segment 170 to adjust the volume of the eluted nucleic acid solution to 50 µl and clamp 370 can then close against the tubule to complete the DNA extraction process.

5. Nucleic Acid Amplification and Detection. The nucleic acid solution can then be transferred to segment 180, mixed, and incubated with UNG 280 at 37° C. for 5 minutes to degrade any contaminant PCR products that may have been present in the biological sample. After the incubation, the temperature may be increased to 95° C. to denature DNA and UNG for 2 minutes. The nucleic acid solution can then be transferred to segment 190, and mixed with PCR reagent 290 at 60° C. to initiate hot start PCR. A typical 2-temperature, amplification assay of 50 cycles of 95° C. for 2 seconds and 60° C. for 15 seconds can be conducted by setting segment 180 at 95° C. and segment 190 at 60° C., and transferring the reaction mixture between the segments alternately by closing and opening actuator 382 and 392. A typical 3-temperature, amplification assay of 50 cycles of 95° C. for 2 seconds, 60° C. for 10 seconds, and 72° C. for 10 seconds can be conducted by setting segment 170 at 95° C., segment 180 at 72° C. and segment 190 at 60° C., and alternately transferring the reaction mixture among the segments by closing and opening the actuators 372, 382 and 392. A detection sensor 492, such as a photometer can be mounted on the block 394 to monitor real-time fluorescence emission from the reporter dye through a portion of the tubule wall. After an assay is complete, the test results can be reported and the sample can be transferred to segment 198 through the pressure gate 194 by compressing segment 190 for further processing.

Figure 8:
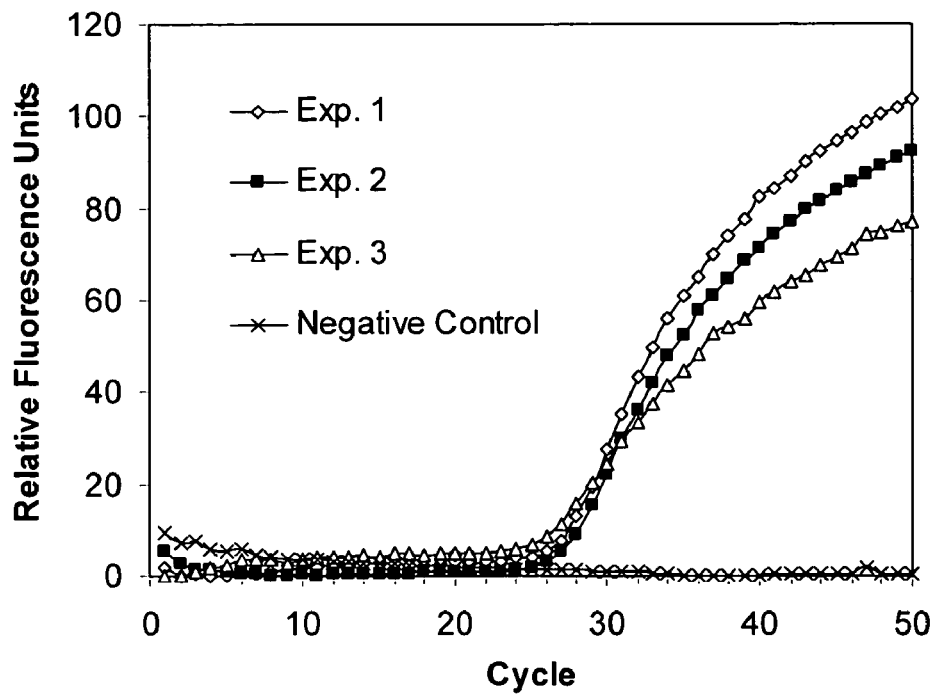
FIGS. 8-10 are graphs of experimental data generated using selected exemplary embodiments of the disclosed devices and methods.

Ten microliters of fresh Ethylenediamine Tetraacetic Acid (EDTA)-treated human whole blood were loaded into a pre-packed sample tube and processed on an analyzer as described in the text. Detection was accomplished with a VIC™-labeled TaqMan Minor Groove Binder probe complimentary to the wild-type hemochromatosis (HFE) gene and a FAM-labeled TaqMan Minor Groove binder probe complementary to the C282Y mutant. FIG. 8 shows the results of three independent experiments, and a negative control in which template DNA was omitted. As these samples contained only wild-type HFE alleles, only the VIC fluorescence trace is shown.

Example 2

Genomic DNA Isolation and Detection from Swab Sample

DNA isolation and DNA sequence detection can be performed in a tube 1, including a flexible tubule 10 having nine segments separated by peelable seals and containing pre-packed reagents, and a cap 20, having a waste reservoir 22 housed therein and additionally a swab protruding from the cap opening. All pre-packed reagents may be identical to that in Example 1, except that sub-segment one 121 of the second segment 120 may contain 50 µl PBS dilution buffer.

The swab on cap 20 can be used to collect a sample from the oral cavity, a surface, or other swabable samples known to those skilled in the art. After collection, the cap can be mated to the tubule, introducing the swab sample to the first segment 110. The tubule can then be inserted into an analyzer. All clamps, except the first clamp 310, may be closed on the tubule. The second actuator 322 can compress the second segment 120 (subsegments 121 and 122) to break the peelable seal 125 and mix PBS 221 with proteinase K 222. The second clamp 320 can then open, and the second actuator compress the second segment to open the peelable seal and move the PBS and proteinase K reagents into the first segment 110. The clamp 320 can close and the first actuator 312 alternately compress and releases to elute the swab sample from the swab tip. After the sample is eluted, the first actuator 312 can compress the first segment 110 and the clamp 320 and second actuator 322 can open to allow the transfer of the eluted sample into the second segment. The second actuator 322 can then compress on the second segment 120 to adjust the volume of eluted sample to about 50 µl, and the second clamp 320 can then compress the tubule to close the segment. All subsequent sample processing steps are similar to that described in Example 1.

Figure 9:
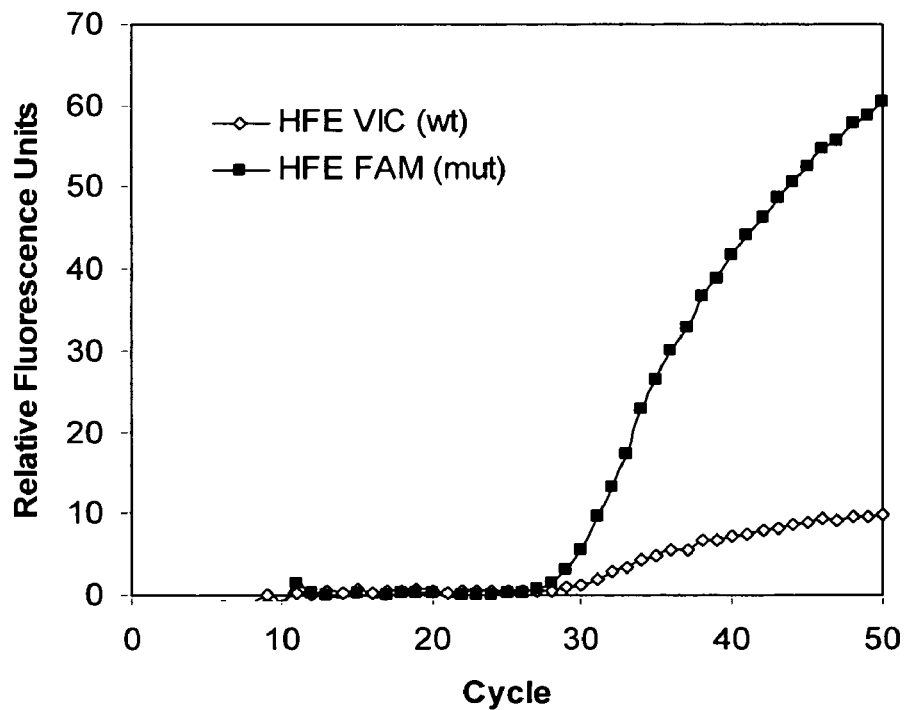

A rayon-tipped sterile swab (Copan, Italy) was scraped against the inside of donor's cheek to harvest buccal epithelial cells. Swab was dipped into 20 µl PBS and stirred briskly to suspend cells. Ten microliters of suspended cells were loaded into a pre-packed sample tubule and processed in an analyzer as described in the text. Detection was accomplished with a VIC-labeled TaqMan Minor Groove Binder probe complimentary to the wild-type HFE gene, and a FAM-labeled probe complimentary to the 282Y mutant of the HFE gene (FIG. 9).

Example 3

Bacterial DNA Isolation from Plasma

DNA isolation and DNA sequence detection from plasma can be performed in a tube 1, including a flexible tubule 10 having nine segments separated by peelable seals and containing pre-packed reagents, and a cap 20, having a waste reservoir 22 housed therein. All pre-packed reagents can be identical to that in example 1, except that sub-segment one 121 of the second segment 120 can contain 50 µl PBS dilution buffer, the third segment 130 can contain 100 µl of lysis buffer 230, and the fourth segment 140 can contain 500 µg of silica magnetic beads suspended in 130 µl of isopropanol. For bacterial DNA detection, over 10 µl of plasma may be loaded into the first segment 110. The sample can then be processed using the pre-packed reagents with the sample processing steps described in Example 1.

Figure 10:
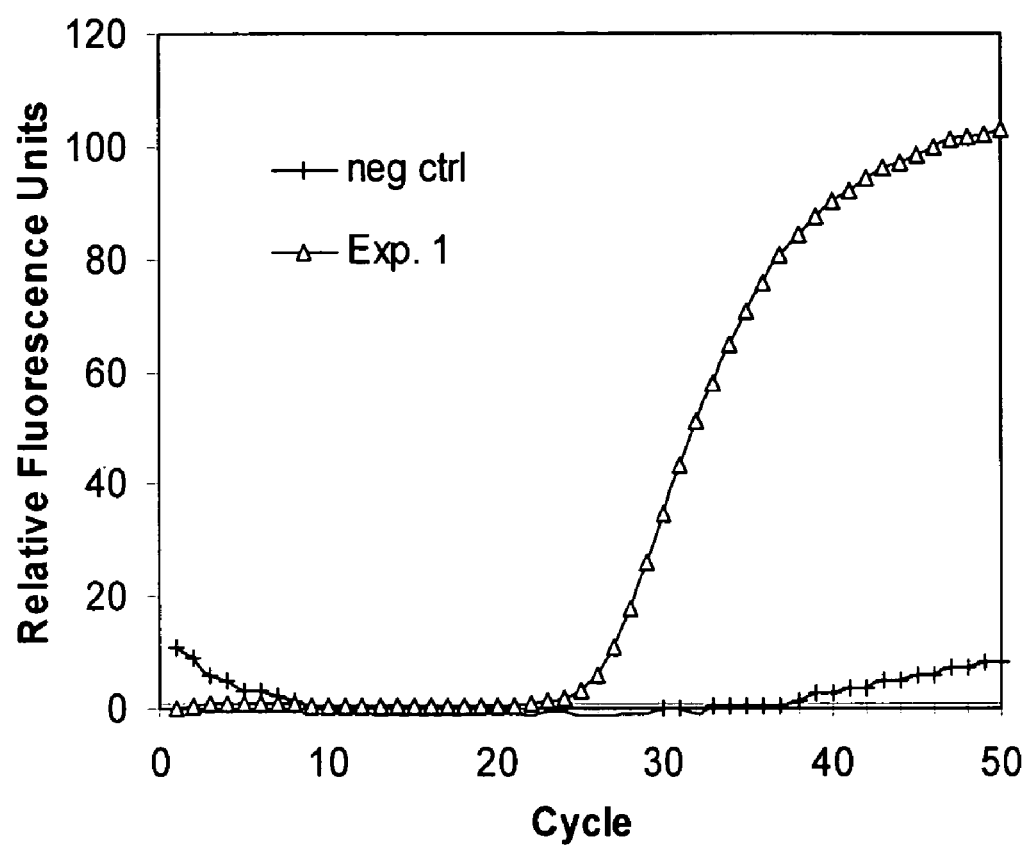

Approximately $10^5$ *E. coli* O157:H7 cells were diluted to a volume of 10 µl in human plasma used for the assay. DNA extraction and detection were performed in the analyzer as described. A FAM-labeled probe recognizing the Stx1 gene of O157:H7 was used for detection. FIG. 10 shows the results with a negative control in which *E. coli* O157:H7 DNA was omitted.

Example 4

Viral RNA Isolation and Detection from Plasma

RNA isolation and RNA sequence detection from plasma can be performed in a tube 1, including a flexible tubule 10 having nine segments separated by peelable seals and containing pre-packed reagents, and a cap 20, having a waste reservoir 22 housed therein. All pre-packed reagents can be identical to that in Example 3, except that the fourth segment 140 can contain either a silica membrane, silica sheet, or silica fiber mesh sized to fit entirely within the segment, as well as 130 µl of isopropanol; and the ninth segment 190 can contain dried RT-PCR reagents 290 which can include 10 nmol of each one of; dATP, dCTP, and dGTP; 20 nmol dUTP, 2.5 µmol of KCl, 200 nmol of $MgCl_2$, 1-5 units of Tth DNA polymerase, and 20-100 pmol of each of the oligonucleotides primer, and 6-25 pmol of TaqMan probe, with or without 1-5 units of Taq DNA polymerase.

For viral nucleic acid isolation and detection, over 50 µl of plasma can be loaded into the first segment 110. The sample can then be processed using the pre-packed reagents with the sample processing steps described in Example 1, with the exception of a modified nucleic acid capture step and an additional reverse transcription step. For the nucleic acid capture step, the fourth clamp 340 may open and the fourth actuator 342 may compress the fourth segment 140 to open the peelable seal and allow the lysate 230 to come into contact with the silica membrane in isopropanol 240 in segment 130. The actuators 332 and 342 can alternately compress their respective segments to agitate and incubate the mixture for 5 minutes at room temperature to facilitate nucleic acid binding to the silica membrane. Following nucleic acid capture, the actuator 342 can compress the segment 140 and the liquid waste can be moved to the waste reservoir. The clamp 330 can close and actuators 332, 342, and 352 can form a flow channel in segments 130, 140, and 150 to allow the ethanol wash buffer to wash the substrate. All subsequent sample processing steps can be the same as Example 3. The additional reverse transcription step may occur prior to PCR amplification and includes incubation of the extracted RNA with RT-PCR reagents in the ninth segment 190 at 65° C. for 10 minutes.

Example 5

Bacterial DNA Isolation and Detection from Whole Blood

DNA isolation and DNA sequence detection from whole blood can be performed in a tube 1, including a flexible tubule 10 having nine segments separated by peelable seals and containing pre-packed reagents, and a cap 20, having a waste reservoir 22 housed therein. Sub-segment one 121 of the second segment 120 may contain 50 µl PBS dilution buffer, the third segment 130 may contain 100 µl of lysis buffer 230, and the fourth segment 140 may contain 10 µg of magnetic beads such as Dynabeads™ (Dynal Biotech), conjugated to $10^4$ to $10^7$ copies of a peptide nucleic acid (PNA) probe, suspended in hybridization buffer (100 µl of 2×SSC/0.1 M EDTA). All other pre-packed reagents can be the same as that described in Example 1.

For bacteria nucleic acid isolation and detection, over 50 µl of whole blood can be loaded into the first segment 110. The sample can then be processed using the pre-packed reagents with the sample processing steps described in Example 1, with the exception of a modified nucleic acid capture step. For the nucleic acid capture step, the fourth clamp 340 opens and the fourth actuator may compress the fourth segment 140 to open the peelable seal and mix the PNA-coupled magnetic beads suspended in hybridization buffer 240 with the lysate in segment 130. The actuators 322 and 332 with an adjacent actuator 312 or 342 may alternately compress their respective segments to agitate and incubate the mixture for 15 minutes at room temperature to facilitate DNA hybridization to the PNA probes coupled to magnetic beads. The sample can then be processed using the pre-packed reagents with the sample processing steps described in Example 1.

Example 6

Viral RNA Isolation and Detection from Whole Blood

Viral RNA isolation and RNA sequence detection from plasma can be performed in a tube 1, including a flexible tubule 10 having nine segments separated by peelable seals and containing pre-packed reagents, and a cap 20, having a waste reservoir 22 housed therein. All pre-packed reagents may be identical to that in Example 5, except that the ninth segment 190 may contain dried RT-PCR reagents 290 which may include 10 nmol of each one of; dATP, dCTP, and dGTP; 20 nmol dUTP, 2.5 µmol of KCl, 200 nmol of $MgCl_2$, 1-5 units of Taq DNA polymerase, 1-5 units of Tth DNA polymerase, and 20-100 pmol of each of the oligonucleotide primers, and 6-25 pmol of TaqMan probe. For viral RNA isolation and detection, over 50 µl of whole blood is loaded into the first segment 110. The sample can then be processed using the pre-packed reagents with the sample processing steps described in Example 1, with the exception of an additional reverse transcription step, prior to amplification, in which the extracted RNA is incubated with RT-PCR reagents in the ninth segment 190 at 65° C. for 10 minutes.

Example 7

Bacterial Isolation using Immunomagnetic Enrichment from Whole Blood

Bacterial DNA isolation and DNA sequence detection from whole blood can be performed in a tube 1, including a flexible tubule 10 having nine segments separated by peelable seals and containing pre-packed reagents, and a cap 20, having a waste reservoir 22 housed therein. The second segment 120 may contain dry magnetic beads, such as Dynabeads, coated with a capture antibody specific for a bacterial epitope. The third segment 130 may contain 100 µl of PBS buffer 230 used to control the sample pH and dilute the red blood cell concentration to ensure efficient binding by the capture antibody. The fourth segment 140 may contain red blood cell lysis buffer including dry salts (1 µmol $KHCO_3$, 15 µmol $NH_4Cl$) and 100 µl of 0.1 mM EDTA, pH 8.0 buffer housed in two sub-segments separated by peelable seal. The fifth segment 150 and sixth segment 160 may contain 80 µl of PBS wash buffer, respectively. All other pre-packed reagents are identical to that in Example 1.

For bacterial detection in whole blood, over 50 µl of whole blood can be loaded into the first segment 110. The tubule is then closed by a cap 20 and inserted into an analyzer. Sample processing includes the following steps.

1. Target Cell Capture. All clamps, except the first clamp 310, may be closed on the tubule. The first actuator 312 may compress on the first segment 110 to adjust the volume of blood 210 to about 50 µl remaining in the segment, and then the first clamp 310 may compress the tubule to close the segment. The third actuator 332 can then compress the third segment 130 to break the peelable seal between segment 130 and segment 120 to mix PBS buffer with antibody coupled magnetic beads to reconstitute a capture solution. The second clamp 320 can then open, and the first actuator 312 can compress the segment 110 to move the blood sample to the second segment 120 and third segment 130. The second actuators 322 and third actuator 332 can then alternately compress the segments to mix the capture solution with blood sample while incubating the mixture at 4° C. for 15-30 minutes to facilitate antibody binding to the target cells. Then, a magnetic field generated by a magnetic source 430 can be applied on the segment 130 to capture the beads in suspension. The actuator 322 and 332 can alternately compress segment 120 and 130 to capture beads. After substantially all the beads are immobilized on the wall of segment 130, the actuators and clamps from actuator 332 to clamp 310 can sequentially open and close to move the unbound sample and waste to the waste reservoir 22.

2. Red Blood Cell Lysis. After target capture, the fourth clamp 340 opens and the fourth actuator can compress the fourth segment 140 to reconstitute the red blood cell lysis buffer and move the buffer to the segment 230. The magnetic field generated by a magnetic source 430 can be removed to allow bead re-suspension. The actuator 322 and 332 can alternately compress their respective segments to agitate and incubate the mixture for 5 minutes at room temperature to facilitate the lysis of red blood cells remaining in the sample. Then, the magnetic field can be applied to the segment 130 to capture the beads in suspension. After substantially all the beads are immobilized on the wall of segment 130, the unbound sample and waste can be moved to the waste reservoir 22.

3. Wash. Two wash processes can follow the binding step, both may use PBS wash buffer pre-packed in segments 150 and 160. Wash may occur by dilution-based wash using the process described above.

4. Nucleic Acid Elution. Elution can occur by the process described in Example 1. The beads suspension can be incubated at 95° C. under stationary, flow or agitation conditions for 2-5 minutes to lyse the captured target cells and release DNA.

5. Nucleic Acid Amplification and Detection. Real-time PCR detection may occur by the same process as that described in Example 1.

Example 8

Viral RNA Isolation using Immunomagnetic Enrichment from Whole Blood

Viral RNA isolation and sequence detection from whole blood can be performed in a tube 1, including a flexible tubule 10 having nine segments separated by peelable seals and containing pre-packed reagents, and a cap 20, having a waste reservoir 22 housed therein. All pre-packed reagents can be identical to those in Example 5, except that the second segment 120 may contain dry magnetic beads, such as Dynabeads, coated with a capture antibody specific for a viral epitope, and the ninth segment 190 may contain dried RT-PCR reagents 290 which may include 10 nmol of each one of dATP, dCTP, and dGTP; 20 nmol dUTP, 2.5 µmol of KCl, 200 nmol of $MgCl_2$, 1-5 units of Taq DNA polymerase, 1-5 units of Tth DNA polymerase, and 20-100 pmol of each of the oligonucleotide primers, and 6-25 pmol of TaqMan probe. For viral RNA isolation and sequence detection, over 50 µl of whole blood can be loaded into the first segment 110. The sample can then be processed using the pre-packed reagents with the sample processing steps described in Example 7, with the exception of a modified target capture step and an additional reverse transcription step. For the target capture step, virion capture by antibody-coupled magnetic beads can be performed at room temperature for 5 minutes in segments 120 and 130. The reverse transcription step may occur prior to amplification, and includes incubation of the extracted RNA is with RT-PCR reagents in the ninth segment 190 at 65° C. for 10 minutes.

Example 9

Multiplex Genotyping of Human DNA with Padlock Probes and Melting Curve Analysis DNA isolation and DNA sequence detection from whole blood may be performed in a tube 1, including a flexible tubule 10 having nine segments separated by peelable seals and containing pre-packed reagents, and a cap 20, having a waste reservoir 22 housed therein. All pre-packed reagents may be identical to those listed in Example 1, with the exception of the eighth segment 180 and the ninth segment 190. The eighth segment 180 may include two sub-segments separated by peelable seal; the first sub-segment may contain dry padlock probes and T4 DNA ligase 280, and the second sub-segment may contain dry exonucelase I and exonuclease III. The ninth segment 190 may contain dry UNG and PCR reagents 290 (which can include 200 µmol of each one of the 3 dNTPs, 100 pmol of each of the oligonucleotides used by PCR, 400 µmol dUTP, 1 nmol of KCl, 0.1 nmol of $MgCl_2$, 5 units of Taq DNA polymerase and optionally 12.5 pmol of TaqMan probe or molecular beacon).

For genotyping, over 10 µl of whole can be loaded into the first segment 110. The sample can then be processed using the pre-packed reagents with the sample processing steps described in Example 1, with the exception of the nucleic acid amplification and detection step. After nucleic acid extraction is complete in the seventh segment 170, actuator 372 may adjust the volume of nucleic acid solution in segment 170 to approximately 5-15 µl, while the remainder of the nucleic acid solution is held in segment 160, segregated from segment 170 by clamp 370. The actuator 372 may then compress on segment 170 to burst the peelable seal between the segment 170 and 180, while maintaining the peelable seal between the first and second sub-segments of segment 180. The extracted nucleic acids may be mixed with T4 DNA ligase and padlock probes in the first sub-segment of segment 180, and the mixture may be moved to segment 170. The remaining nucleic acid solution held in segment 160 may also be moved to segment 170. The nucleic acid solution, padlock probe and T4 ligase may be incubated in segment 170 at 37° C. for 15 minutes. The mixture may then be moved to the eighth segment 180 to break the peelable seal of the second sub-segment of segment 180 to incubate the nucleic acids with Exonuclease I and Exonuclease III at 37° C. for 5 minutes to degrade all linear DNA fragments. After incubation, the solution may be heated to 95° C. in the eighth segment 180 to inactivate the Exonucelases and T4 ligase. The solution can then be transferred to the ninth segment 190 to mix with dry UNG and PCR reagents. The UNG degrades any contaminant PCR products that may have been present when the sample was introduced, and linearizes the circularized padlock probes to facilitate the amplification of the reporter sequences. PCR amplification may be performed as described in Example 1. A detection sensor 492 mounted on the block 394 can monitor real-time fluorescence emission from the reporter dye through a portion of the tubule wall. Melting curve analysis can be performed to identify the targets. Alternatively, the sample can be transferred to segment 198 through the pressure gate 194 for further detection on a nucleic acid microarray or other detection techniques known to those skilled in the art.

Example 10

Live Bacterial Spore Isolation and Germination

DNA isolation and DNA sequence detection from surface swab spore sample can be performed in a tube 1, including a flexible tubule 10 having nine segments separated by peelable seals and containing pre-packed reagents, and a cap 20, having a waste reservoir 22 housed therein and additionally a swab protruding from the cap opening. The first segment 110 of the tubule may include two sub-segments separated by a peelable seal; the first sub-segment can be adapted to housing a swab sample, and the second sub-segment may contain 80 µl of PBS wash buffer having a pH appropriate to permit efficient binding of the spores by the capture antibody. The second segment 120 may contain solid substrate whereon anti-spore antibodies may be coated; wherein the antibodies have a high affinity for epitopes on the spore and low affinity for epitopes on the germinated cell. The second segment may be further pre-packed with a volume of a gas to facilitate breaking of the peelable seal between segments 120 and 110. The third segment 130 may contain 50 µl of spore germination reagents 230 which may include Brain Heart infusion medium (Difco), His 50 mM, Tyr 1 mM, Inosine 2 mM, Ala 200 mM, and Ser 200 mM. The fourth segment 140 may contain 50 µl of lysis buffer 240 containing chaotropic salts including 4.7 M guanidinium hydrochloride, 10 mM urea, 10 mM Tris HCl, pH 5.7, and 2% triton X-100. The fifth segment 150 may contain 500 µg of magnetic silica beads 240, such as MagPrep™ beads (Merck & Co), suspended in 80 µl of isopropanol. The sixth segment 160 may contain 80 µl of wash buffer (50% ethanol 250, 20 mM NaCl, 10 mM Tris HCl, pH 7.5). The seventh segment 170 may contain 80 µl of 20 mM MES buffer 270, pH 5.3. The eighth segment 180 may contain 80 µl elution buffer 280 (10 mM Tris HCl, pH 8.5). The ninth segment 190 may contain dry UNG and dried PCR reagents 290 (which may include 10 nmol of each one of the dATP, dCTP, and dGTP; 20 nmol dUTP, 2.5 µmol of KCl, 200 nmol of $MgCl_2$, 1-5 units of Taq DNA polymerase, and 20-100 pmol of each of the oligonucleotide primers, and 6-25 pmol of TaqMan probe).

For live spore detection, the swab integrated into the cap 20 can be used to collect a sample. After collection, the cap can be mated to the tubule, introducing the swab sample to the first segment 110. The tubule can then be inserted into an analyzer. Sample processing may include the following steps.

1. Spore germination. All clamps, except the first clamp 310, maybe closed on the tubule. The first actuator 312 compresses on the first segment 110 to burst the peelable seal between the first and second sub-segment of segment 110 to release the PBS wash buffer. The first actuator 310 may then alternately compress and decompresss the segment 110 to wash spores from the swab head using the PBS buffer. After suspension of the spores in PBS, actuator 322 may compress segment 120 to burst the peelable seal between segments 110 and 120 and allow the spore suspension to move to segment 120. Clamp 320 can close and actuator 322 can alternately compress segment 120 to facilitate binding of the spore to the antibody. After incubation, the liquid waste can be moved to the waste reservoir. Actuator 332 can then compress segment 130 to burst the peelable seal between segments 120 and 130 to allow the germination solution to be incubated with the captured spores at 37° C. for 13 minutes with agitation in segment 120. Germinated cells will not be bound by the spore-specific antibody and will be suspended in solution.

2. Nucleic Acid Capture. After germination, the fourth clamp 340 can open and the fourth actuator 342 compress the fourth segment 140 to open the peelable seal and mix the lysis buffer with the germinated cells. Then the fifth clamp 350 can open and the fifth actuator 352 compress segment 150 to move magnetic silica beads suspended in isopropanol 240 to segment 130 to mix with the lysate. The actuators 332 and 342 can alternately compress their respective segments to agitate and incubate the mixture for 5 minutes at room temperature to facilitate DNA binding to the magnetic silica beads. Then, the magnetic field generated by a magnetic source 430 can be applied on the segment 130 to capture the beads in suspension. The actuator 332 and 342 can alternately compress segment 130 and 140 to capture beads. After substantially all the beads are immobilized on the wall of segment 130, the unbound sample and waste can be moved to the waste reservoir 22.

3. Wash. Ethanol wash buffer in segment 160 and MES buffer in segment 170 can be used for washing the immobilized beads. A dilution based wash can be performed in segments 120 and 130 by actuators 322 and 332 as described in Example 1. Alternatively, a thin-layer flow based wash can be performed in segments 120, 130, and 140 by actuators 322, 332, and 342 as described in Example 1.

4. Nucleic acid elution. Elution buffer 270 can be moved from segment 180 to 130 for DNA elution as described in Example 1.

5. Nucleic Acid Amplification and Detection. The nucleic acid solution can then be transferred to segment 190 and mixed with UNG and dry PCR reagents. Incubation of the reaction mixture at 37° C. for 5 minutes allows UNG to degrade any contaminant PCR products. After the incubation, the reaction mixture can be transferred to segment 180 for denaturation at 95° C. for 2 minutes. The nucleic acid solution can then be transferred to segment 190, for incubation at 60° C. to initiate hot start PCR. A typical 2-temperature, amplification assay of 50 cycles of 95° C. for 2 seconds and 60° C. for 15 seconds can be conducted by setting segment 180 at 95° C. and segment 190 at 60° C., and transferring the reaction mixture between the segments alternately by closing and opening actuator 382 and 392. A typical 3-temperature, amplification assay of 50 cycles of 95° C. for 2 seconds, 60° C. for 10 seconds, and 72° C. for 10 seconds can be conducted by setting segment 170 at 95° C., segment 180 at 72° C. and segment 190 at 60° C., and alternately transferring the reaction mixture among the segments by closing and opening the actuators 372, 382 and 392. A detection sensor 492, such as a photometer can be mounted on the block 394 to monitor real-time fluorescence emission from the reporter dye through the tubule wall. After an assay is complete, the test results can be reported and the sample can be transferred to segment 198 through the pressure gate 194 by compressing segment 190 for further processing.

Example 11

Multiplex Genotyping of Human DNA from Solid Tissue Sample

In a eleventh embodiment, DNA isolation and DNA sequence detection from solid tissue sample can be performed in a tube 1, including a flexible tubule 10 having nine segments separated by peelable seals and containing pre-packed reagents, and a cap 20, having a waste reservoir 22 housed therein. The first segment 110 of the tubule can be adapted to receive a solid tissue sample and have tough walls with micro-teeth-like inner surfaces to facilitate tissue grinding. The second segment 120 can contain 250 μg dry proteinase K 222. The third segment 130 can contain 100 μl of lysis buffer 230 containing chaotropic salts including 4.7 M guanidinium hydrochloride, 10 mM urea, 10 mM Tris HCl, pH 5.7, and 2% triton X-100. The fourth 140, fifth 150, sixth 160 and the seventh 170 segments can contain the same reagents as in Example 1. The eighth segment 180 can include two sub-segments separated by a peelable seal; the first sub-segment may contain dry padlock probes and T4 DNA ligase 280, and the second sub-segment may contain dry exonuclease I and exonuclease III. The ninth segment 190 may contain dry UNG and PCR reagents 290 (which may include 200 μmol of each one of the 3 dNTPs, 100 pmol of each of the oligonucleotides used by PCR, 400 μmol dUTP, 1 nmol of KCl, 0.1 nmol of $MgCl_2$, 5 units of Taq DNA polymerase and optionally 12.5 pmol of TaqMan probe).

For a mutation detection assay, a 1 mg to 50 mg solid tissue sample can be loaded into the first segment. The tubule can then be closed by a cap 20 and inserted into an analyzer. Subsequently, all clamps can be closed on the tubule. The clamp 330 can open and the third actuator 332 compress the third segment 130 to break the peelable seal between segment 120 and 130 to mix the lysis buffer 230 with proteinase K. The second clamp 320 can then open, and the second actuator can compress the second segment to open the peelable seal and introduce the lysis solution to the solid tissue sample in segment 110. The second clamp 320 can close, and the first actuator 312 can compress and decompress the segment 110, facilitating the homogenization of the solid tissue sample with the micro-teeth on the tubule wall surface. The thermal element contacting segment 110 may be set to 50-68° C. to increase the efficiency of proteinase digestion. After the tissue sample has been sufficiently homogenized, the homogenate can be moved to segment 120 and the magnetic silica beads suspended in isopropanol of segment 140 can be moved to segment 130. The actuators 322 and 332 can alternately compress their respective segments to mix the homogenate with the bead suspension to facilitate DNA binding to the magnetic silica beads. Then, the magnetic field generated by a magnetic source 430 can be applied to the segment 130 to capture the beads in suspension. The actuators 322 and 332 can alternately compress segments 120 and 130 to capture beads in the magnetic field. As an alternative, the actuator 332 can compress segment 130 to form a flow-channel, and two flanking actuators 322 and 342 can compress the respective segments alternately to increase the capture efficiency. After substantially all the beads have been immobilized on the wall of segment 130, the actuators and clamps from actuator 342 to clamp 310 can be sequentially opened and closed to move the unbound sample and waste to the waste reservoir 22. The subsequent wash and nucleic acid elution steps can occur by the process described in Example 1. Nucleic acid amplification and detection can occur by the padlock probe assay process as described in Example 9.

Example 12

Plasma Separation and Virus Detection from Whole Blood

In a twelfth embodiment, RNA isolation and sequence detection from whole blood can be performed in a tube 1, including a flexible tubule 10 having nine segments separated by peelable seals and containing pre-packed reagents, and a cap 20, having a waste reservoir 22 housed therein. The first segment 110 of the tubule can include two sub-segments separated by a peelable seal; the first sub-segment can be adapted to receive a whole blood sample, and second sub-segment can contain one of a coagulant, such as thrombin, or a dry multi-valent anti-red blood cell antibody. The first segment further can contain at its base in the second sub-segment one or a plurality of embedded filter bags of pore size preferably between 1 µm to 10 µm. Filter pore size can be such that substantially no blood cells may pass and only plasma may pass. The second segment 120 may contain 80 µl PBS dilution buffer. The third segment 130 may contain 250 µg dry proteinase K and 60 µl lysis buffer (4.7 M guanidinium hydrochloride, 10 mM urea, 10 mM Tris HCl, pH 5.7, and 2% triton X-100) housed in two sub-segments separated by a peelable seal. The fourth 140, fifth 150, sixth 160, seventh 170, and eighth 180 segments may contain the same reagents as in Example 1. The ninth segment 190 may contain dried RT-PCR reagents 290 which can include 10 nmol of each one of: dATP, dCTP, and dGTP; 20 nmol dUTP, 2.5 µmol of KCl, 200 nmol of $MgCl_2$, 1-5 units of Taq DNA polymerase, 1-5 units of Tth DNA polymerase, and 20-100 pmol of each of the oligonucleotides primer, and 6-25 pmol of TaqMan probe.

For plasma separation within the tubule, approximately 300 µl of whole blood can be loaded into the first segment 110. All clamps can be closed, and actuator 312 can compress segment 110 to burst the peelable seal between the sub-segments and allow the mixing of the blood sample with dry multi-valent anti-red blood cell antibody or coagulant. Actuator 312 can alternately compress and decompression the segment 110 to facilitate the binding of antibody to red blood cells and the formation of cell clusters. Actuator 322 can compress segment 120 to burst the peelable seal between segment 120 and 110 and to move the dilution buffer to segment 110 to mix with blood sample. After a sufficient quantity of red blood cells have aggregated, actuator 312 can gently compress segment 110 to drive the blood sample through the embedded filter, while actuator 322 can slowly decompress segment 120 to create suction from the other side of the filter. Following plasma separation, clamp 320 can be closed and actuator 332 can compress segment 130 to reconstitute dry proteinase K in the lysis buffer. Clamp 330 can then open and actuator 322 can compress segment 120 to mix the plasma sample with the lysis buffer and incubate the mixture at 50° C. for 5 minutes in segment 130. For DNA viruses, the subsequent nucleic acid capture, wash, elution, and amplification and detection steps can be the same as that described in Example 1. A reverse transcription step may be added prior to amplification, in which the extracted RNA is incubated with RT-PCR reagents in the ninth segment 190 at 65° C. for 10 minutes.

Example 13

Genomic DNA Isolation and Detection from Whole Blood Collected on Cotton Based Matrices In a thirteenth embodiment, DNA isolation and DNA sequence detection can be accomplished in a tube 1, including a flexible tubule 10 having four segments separated by peelable seals and containing pre-packed reagents, and a cap 20, which may have a waste reservoir 22 housed therein. The first segment 110 of the tubule can receive the whole blood sample collected on cotton-based matrices, such as Whatman BFC 180 and FTA® paper, Schleicher and Schuell 903™ and IsoCode® paper. The second segment 120 may contain washing buffer including 40 µl of distilled water 220. The third segment 130 may contain 80 µl elution buffer (10 mM Tris HCl, pH 8.5) or distilled water 230. The fourth segment 140 may contain dry UNG and dried PCR reagents 240 (which may contain 10 nmol of each one of the 3 dNTPs: dATP, dCTP, and dGTP; 20 nmol dUTP, 2.5 µmol of KCl, 200 nmol of $MgCl_2$, 1-5 units of Taq DNA polymerase, and 20-100 pmol of each of the oligonucleotide primers, and 6-25 pmol of TaqMan probe). The end of segment 140 can be permanently sealed.

For genotyping, whole blood, such as collected by a finger prick or other means may be absorbed onto cotton-based matrices 30 attached to sample tubule cap 20 through connector 36. The tube can then be closed by a cap 20 and inserted into an analyzer. Sample processing may include the following steps.

1. Sample Lysis. All clamps, except the first clamp 310, may be closed on the tubule. The first actuator 312 may compress the first segment 110 to adjust the distance of the actuator 312 to the cotton-based matrices 30 in the segment, and then the first clamp 310 may compress the tubule to close the segment. The first segment can be incubated at 95° C. for 5 minutes to dry the blood sample. Then, the segment temperature may be allowed to cool to room temperature. The drying process can lyse whole blood cells and enhance the binding of plasma proteins and PCR inhibitors to the cotton matrices. The incubation temperature can be maintained by contact between the tubule and the thermal elements incorporated within the actuators and/or blocks opposing the actuators.

2. Wash. A wash process can follow the heating process in order to remove washable residuals and PCR inhibitors from the matrices and the segments that would be used for further sample process. In this embodiment, a dilution based washing or a thin-layer flow based washing can be used. For dilution based wash, Clamps 320 can first open, and then actuator 322 can close to move the wash buffer 220 to segment 210, followed by the closing of clamp 320. The first actuator 312 can agitate the cotton-based matrices through a repeated compressing and releasing action to release unbound plasma protein components and PCR inhibitor for 3 minutes at room temperature. After completing the wash, the wash buffer can be moved from segment 110 to waste reservoir 22 housed in the cap 20. Actuator 312, clamps 310 and 320 can be gently released to form a thin-layer flow channel through segment 110. Actuator 322 can compress gently on segment 120 to generate a certain inner pressure to ensure a substantially uniform gap of the thin-layer flow channel. Actuator 322 can then compress the tubule to generate essentially laminar flow of the wash buffer through the flow channel. When the wash is completed, the actuators and clamps can compress on the segments and substantially all the waste may be moved to the waste reservoir 22.

3. Nucleic Acid Elution. The elution buffer 230 may then be moved from segment 130 to 110 by using a similar process as mentioned before. The cotton-based matrix can be incubated at 95° C. under stationary, flow or agitation conditions for 2 minutes. The eluate can then be moved to segment 130. The actuator 332 can compress segment 130 to adjust the volume of the eluted nucleic acid solution to 50 µl and clamp 330 can then close against the tubule to complete the DNA extraction process.

4. Nucleic Acid Amplification and Detection. The nucleic acid solution can then be transferred to segment 140, mixed, and incubated with UNG and PCR reagent 240 at 37° C. for 5 minutes to degrade any contaminant PCR products that may have been present when the sample was introduced. After the incubation, the temperature may be increased to 95° C. to denature DNA for 2 minutes followed by PCR reaction. A typical 2-temperature, amplification assay of 50 cycles of 95° C. for 2 seconds and 60° C. for 9-15 seconds can be conducted by setting segment 180 at 95° C. and segment 190 at 60° C., and transferring the reaction mixture between the segments alternately by closing and opening actuator 332 and 342. A typical 3-temperature, amplification assay of 50 cycles of 95° C. for 2 seconds, 60° C. for 8-10 seconds, and 72° C. for 8-12 seconds can be conducted by setting segment 120 at 95° C., segment 130 at 72° C. and segment 140 at 60° C., and alternately transferring the reaction mixture among the segments by closing and opening the actuators 322, 332 and 342. A detection sensor, such as a photometer 492, can be mounted on the block 344 to monitor real-time fluorescence emission from the reporter dye through the tubule wall.

All of the patents and publications cited herein are hereby incorporated by reference.

We claim:

1. A sample processing apparatus, comprising:
    a tubule, comprising:
        a proximal end having an opening through which a sample is introducible;
        a distal end; and
        at least a first segment containing at least one substance capable of specific binding to a preselected component of a sample when the sample is added to the tubule, a second segment distal to the first segment and containing a wash reagent, and a third segment distal to the second segment and containing an amplification reagent, each of which segments is:
        defined by the tubule;
        fluidly isolated, at least in part by a fluid-tight seal formed by a bonding of opposed wall portions of the tubule to one another such that:
            (a) the seal is broken by application of fluid pressure on a segment that is fluidly isolated in part by the seal; and
            (b) the seal is capable of being clamped where the opposed wall portions of the tubule are bonded, without breaking the seal, to prevent the seal from being broken by application of fluid pressure on a segment that is fluidly isolated in part by the seal;
        so expandable as to receive a volume of fluid expelled from another segment; and
        so compressible as to contain substantially no fluid when so compressed;
    a cap for closing the opening, the cap containing a chamber in fluid communication with the tubule, and the cap permitting free escape of gasses but retaining all liquid volumes and infectious agents in the tube;
    a rigid frame to which the tubule's proximal and distal ends are held; and
    an integral tubule tensioning mechanism or an attachment of the tubule to the frame that pulls the tubule sufficiently taut so as to facilitate compression and flattening of the tubule.

2. The apparatus of claim 1, wherein at least a portion of the tubule is transparent.

3. The apparatus of claim 1, further comprising at least one pressure gate in fluid communication with at least one segment.

4. The apparatus of claim 1, further comprising at least one filter in the tubule.

5. The apparatus of claim 1, wherein the preselected component is nucleic acid.

6. The apparatus of claim 5, wherein the substance capable of specific binding to nucleic acid includes at least one of an antibody, nucleic acid, peptide nucleic acid, phosphothioate nucleic acid, silica coated surface, electrostatically charged surface, and enzyme.

7. The apparatus of claim 6, wherein the substance capable of specific binding to nucleic acid has a preselected amino acid or base sequence.

8. The apparatus of claim 1, wherein the substance comprises at least one of a receptor, a ligand, an antibody, an antigen, a nucleic acid probe, a peptide nucleic acid probe, a phosphothioate nucleic acid probe, a bacteriophage, silica, and an electrostatic charged surface.

9. The apparatus of claim 1, wherein the substance is capable of specific binding to a preselected component of at least one of bacteria, virus, parasite, cells, nucleic acid, and spores.

10. The apparatus of claim 9, wherein the substance is capable of specific binding to a preselected component of at least one of *Yersinia pestis, Francisella tularensis, Listeria monocytogenes, Bacillus anthracis, Escherichia coli, Salmonella enteritidis, Campylobacter pylori, Campylobacter jejuni Clostridium perfringens, Staphylococcus aureus, Haemophilus influenzae, Streptococcus pneumoniae, Neisseria meningitides, Vibrio cholerae, Mycobacterium tuberculosis,* and *Mycobacterium leprae.*

11. The apparatus of claim 9, wherein the substance is capable of specific binding to a preselected component of at least one of human immunodeficiency virus 1, human immunodeficiency virus 2, influenza virus, yellow fever virus, dengue virus, hepatitis B virus, hepatitis C virus, cytomegalovirus, Epstein Barr virus, West Nile virus, hantavirus, and small pox.

12. The apparatus of claim 9, wherein the substance is capable of specific binding to a preselected component of at least one of *Plasmodium falciparum, Plasmodium vivax, Plasmodium ovale, Plasmodium malariae, Leishmania tropica, Leishmania donovani, Leishmania infantum, Leishmania major, Leishmania mexicana, Leishmania chagasi, Leishmania brasiliensis,* and *Leishmania amazoniensis.*

13. The apparatus of claim 1, wherein the substance capable of specific binding to a preselected component of a sample is coupled to a solid substrate.

14. The apparatus of claim 13, wherein the substance forms a coating on the solid substrate.

15. The apparatus of claim 13, wherein the solid substrate comprises at least one of beads, a pad, a filter, a sheet, an electrostatic surface, and a portion of a tubule wall surface.

16. The apparatus of claim 13, wherein the substrate comprises at least one of silica beads, magnetic beads, silica magnetic beads, glass beads, nitrocellulose colloid beads, and magnetized nitrocellulose colloid beads.

17. The apparatus of claim 13, wherein the substance comprises silica, and the substrate comprises a filter or a sheet.

18. The apparatus of claim 13, wherein the substrate comprises a pad formed at least in part from an absorbent material comprising at least one of paper, film, filter, foam, mesh, and fiber matrix.

19. The apparatus of claim 13, wherein the substrate is coupled to a tubule wall.

20. The apparatus of claim 1, further comprising a solid substrate which comprises a pad formed at least in part from an absorbent material comprising at least one of paper, film, filter, foam, mesh, and fiber matrix.

21. The apparatus of claim 1, wherein the cap comprises a sample collection device including at least one of a swab, a stick, a scoop, an inoculation loop, a forceps, a dropper, a capillary tube, and a syringe.

22. The apparatus of claim 21, wherein the sample collection device is so disposed in or on the cap as to transfer a sample from the device to the tubule when the cap is positioned in relation to the tubule to close the open end of the tubule.

23. The apparatus of claim 1, wherein the cap comprises a member defining the chamber, and wherein the chamber is expandable.

24. The apparatus of claim 23, wherein a cap wall defines a vent.

25. The apparatus of claim 1, wherein the frame comprises an interface, the interface receiving the proximal end of the tubule.

26. The apparatus of claim 25, wherein the interface also receives the cap, thereby sealing the proximal end of the tubule.

27. The apparatus of claim 1, further comprising at least one of a diluent, suspension reagent, lysis reagent, neutralization reagent, elution reagent, proteolytic reagent, glycosylase, nucleic acid, nuclease, ligase, alcohol, reverse transcription reagent, and germination reagent.

28. The apparatus of claim 27, wherein the tubule comprises an elution reagent that includes at least one of Tris buffer, water, and buffer suitable for polymerase chain reaction.

29. The apparatus of claim 27, wherein the tubule comprises a lysis reagent that includes at least one of a guanidinium salt, a chaotropic salt, a red blood cell lysis reagent, a detergent, a chelator, a spore germination reagent, sodium hydroxide, proteinase K, DNase inhibitor, RNase, RNase inhibitor, anticoagulant, coagulant, a protease, a germinant solution, and a surfactant.

30. The apparatus of claim 27, wherein the tubule comprises a germination reagent including heart brain infusion medium and at least one of L-alanine, inosine, L-phenylalanine, L-Serine and L-proline.

31. The apparatus of claim 1, wherein the segments form a substantially linear array.

32. The apparatus of claim 1, wherein the segments form a contiguous array.

33. A sample processing apparatus, comprising:
a tubule, comprising:
  a plurality of segments, each of which is:
    defined by the tubule;
    fluidly isolated, at least in part by a fluid-tight seal formed by a bonding of opposed wall portions of the tubule to one another such that:
      (a) the seal is broken by application of fluid pressure on a segment that is fluidly isolated in part by the seal; and
      (b) the seal is capable of being clamped where the opposed wall portions of the tubule are bonded, without breaking the seal, to prevent the seal from being broken by application of fluid pressure on a segment that is fluidly isolated in part by the seal;
    separated from adjacent segments only by seals;
    so expandable as to receive a volume of fluid expelled from another segment; and
    so compressible as to contain substantially no fluid when so compressed;
  wherein:
    a segment contains at least one of a lysis reagent and a diluent;
    a segment contains at least a nucleic acid binding reagent;
    a segment contains at least a wash reagent;
    a segment contains at least a nucleic acid eluting regent; and
    a segment contains at least nucleic acid amplification reagents;
  a cap for closing the opening, the cap containing a chamber in fluid communication with the tubule, and the cap permitting free escape of gasses but retaining all liquid volumes and infectious agents in the tube;
  a rigid frame to which the tubule's proximal and distal ends are held; and
  an integral tubule tensioning mechanism or an attachment of the tubule to the frame that pulls the tubule sufficiently taut so as to facilitate compression and flattening of the tubule.

34. The apparatus of claim 1, wherein at least one of the reagents is in a dry format.

35. The apparatus of claim 1, wherein the segments form a contiguous and substantially linear array.

36. The apparatus of claim 1, further comprising at least a fourth segment that (a) is distal to the second segment and (b) contains at least one of an elution reagent, second wash regent, lysis reagent, reverse transcription reagent, a nucleic acid, a nuclease, and glycosylase.

37. The apparatus of claim 1, further comprising at least a fourth segment that (a) is proximal to the first segment and (b) contains at least one of a germination reagent, suspension reagent, lysis reagent, neutralization reagent, diluent, second wash reagent, elution reagent, nucleic acid, and proteolytic reagent.

38. The apparatus of claim 1, further comprising at least a fourth segment that (a) is distal to the third segment and (b) contains at least one of a second amplification reagent, a nuclease, a detection reagent, and a glycosylase.

39. The apparatus of claim 1, further comprising at least a fourth segment that (a) is distal to the first segment and (b) contains at least one of a diluent, suspension reagent, nucleic acid, lysis reagent, second wash reagent, a solid substrate, and alcohol.

40. The apparatus of claim 1, further comprising:
a fourth segment that (a) is proximal to the first segment and (b) contains at least one of a lysis reagent and a diluent; and
a fifth segment that (a) is distal to the second segment, (b) proximal to the third segment, and (c) contains an elution reagent.

41. The apparatus of claim 1, wherein the amplification reagent in the third segment comprises at least one of a nucleic acid polymerase and nucleotide triphosphates.

42. The apparatus of claim 1, wherein the at least one substance capable of specific binding to a preselected component of a sample in the first segment specifically binds nucleic acid.

43. The apparatus of claim 1, wherein the third segment contains a detection reagent.

44. The apparatus of claim 1, wherein the opposed wall portions of the tubule are left free of projections when the seal is broken.

45. The apparatus of claim 44, wherein the segments form a substantially linear array.

46. The apparatus of claim 45, wherein the segments form a contiguous array.

47. The apparatus of claim 1, wherein the cap chamber has a wall that comprises a barrier preventing liquid escape and that defines a waste cavity in fluid communication with the opening.

48. The apparatus of claim 1, wherein the cap chamber has a wall that comprises a vent, and a member preventing liquid escape, and that defines a waste cavity in fluid communication with the opening.

49. The apparatus of claim 1, wherein the cap chamber has a flexible membrane that prevents liquid escape, that defines a waste cavity in fluid communication with the opening, and that is deformable to increase the waste cavity volume.

50. The apparatus of claim 1, wherein a fourth segment distal to the third segment contains a detection reagent.

51. The apparatus of claim 1, wherein the substance capable of specific binding to a preselected component of the sample is, comprises, or is coupled to a solid phase substrate.

52. The apparatus of claim 51, wherein the wash reagent is capable of retaining the preselected component on the solid phase substrate while allowing removal of components of the sample not bound to the substrate.

53. The apparatus of claim 52, wherein the amplification reagent is capable of amplifying the preselected component of the sample.

54. The apparatus of claim 51, wherein the amplification reagent is capable of amplifying the preselected component of the sample.

55. The apparatus of claim 51, further comprising a fourth segment that (a) is distal to the second segment, (b) is proximal to the third segment, and (c) contains an elution reagent capable of eluting the preselect component from the substrate.

56. The apparatus of claim 1, wherein the amplification reagent is capable of amplifying the preselected component of the sample.

57. The apparatus of claim 5, wherein:
the substance capable of specific binding to the preselected component of the sample comprises silica;
the silica is coupled to magnetic beads; and
the amplification reagent comprises at least one of a primer, a nucleotide triphosphate, and an amplification enzyme.

58. The apparatus of claim 1, wherein the segments are prepacked with their respective contents.

59. The apparatus of claim 1, wherein the cap chamber contains a reagent.

60. The apparatus of claim 1, wherein the apparatus comprises the integral tubule tensioning mechanism, and the mechanism comprises cantilever or leaf springs.

61. The apparatus of claim 1, wherein the apparatus comprises the attachment of the tubule to the frame, and the attachment comprises at least one of a seal, a weld, an adhesive joint, and an insert-molding.

62. The apparatus of claim 1, wherein the cap further comprises a filter that permits the free escape of gasses while retaining all liquid volumes and infectious agents in the tube.

63. The apparatus of claim 1, wherein the cap further contains a waste cavity in fluid communication with the tubule.

* * * * *

UNITED STATES PATENT AND TRADEMARK OFFICE
CERTIFICATE OF CORRECTION

| | | |
|---|---|---|
| PATENT NO. | : 7,718,421 B2 | |
| APPLICATION NO. | : 10/773775 | |
| DATED | : May 18, 2010 | |
| INVENTOR(S) | : Shuqi Chen et al. | |

It is certified that error appears in the above-identified patent and that said Letters Patent is hereby corrected as shown below:

Page 2, right col., line 1: change "2003/1013439" to --2003/0134390 A1--

Col. 8, line 14: change "stiffniess" to --stiffness--

Col. 15, line 3: change "nickedcircular" to --nicked circular--

Col. 20, line 6: change "whichE" to --which E--

Col. 24, line 63: change "maybe" to --may be--

Signed and Sealed this

Ninth Day of November, 2010

David J. Kappos
*Director of the United States Patent and Trademark Office*